(12) United States Patent
Zhang et al.

(10) Patent No.: US 12,154,664 B2
(45) Date of Patent: Nov. 26, 2024

(54) SYSTEMS AND METHODS FOR DETERMINING MICROSATELLITE INSTABILITY

(71) Applicant: ILLUMINA, INC., San Diego, CA (US)

(72) Inventors: Shile Zhang, San Diego, CA (US); Alex S. So, San Diego, CA (US); Shannon Kaplan, San Diego, CA (US); Kristina M. Kruglyak, San Diego, CA (US); Sven Bilke, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1427 days.

(21) Appl. No.: 16/191,142

(22) Filed: Nov. 14, 2018

(65) Prior Publication Data

US 2019/0156922 A1    May 23, 2019

Related U.S. Application Data

(60) Provisional application No. 62/652,151, filed on Apr. 3, 2018, provisional application No. 62/587,350, filed on Nov. 16, 2017.

(51) Int. Cl.
| | | |
|---|---|---|
| G16H 10/60 | (2018.01) | |
| C12Q 1/6869 | (2018.01) | |
| C12Q 1/6886 | (2018.01) | |
| G01N 33/50 | (2006.01) | |
| G06F 9/30 | (2018.01) | |
| G16B 20/20 | (2019.01) | |
| G16B 30/20 | (2019.01) | |

(52) U.S. Cl.
CPC ........... *G16H 10/60* (2018.01); *C12Q 1/6886* (2013.01); *G01N 33/50* (2013.01); *G06F 9/3004* (2013.01); *G16B 20/20* (2019.02); *G16B 30/20* (2019.02); *C12Q 1/6869* (2013.01)

(58) Field of Classification Search
None
See application file for complete search history.

(56) References Cited

U.S. PATENT DOCUMENTS

| | | |
|---|---|---|
| 6,172,218 B1 | 1/2001 | Brenner |
| 6,306,597 B1 | 10/2001 | Macevicz |
| 6,969,488 B2 | 11/2005 | Bridgham et al. |
| 7,001,792 B2 | 2/2006 | Sauer et al. |
| 7,057,026 B2 | 6/2006 | Barnes et al. |
| 10,741,269 B2 | 8/2020 | Chudova et al. |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Barr Ost et al. |
| 2007/0166705 A1 | 7/2007 | Milton et al. |
| 2008/0096197 A1* | 4/2008 | Findeisen ............ C12Q 1/6886 435/6.12 |
| 2009/0026082 A1 | 1/2009 | Rothberg et al. |
| 2010/0137143 A1 | 6/2010 | Rothberg et al. |
| 2010/0282617 A1 | 11/2010 | Rothberg |
| 2011/0177517 A1 | 7/2011 | Rava et al. |
| 2012/0095697 A1 | 4/2012 | Halpern et al. |
| 2012/0295267 A1 | 11/2012 | Goel et al. |
| 2014/0066317 A1 | 3/2014 | Talasaz et al. |
| 2015/0347676 A1 | 12/2015 | Zhao et al. |
| 2016/0019338 A1 | 1/2016 | Chudova et al. |
| 2016/0239604 A1 | 8/2016 | Chudova et al. |

FOREIGN PATENT DOCUMENTS

| | | |
|---|---|---|
| AU | 2013204536 A1 | 2/2014 |
| CN | 105722994 A | 6/2016 |
| CN | 105760712 A | 7/2016 |
| CN | 105830077 A | 8/2016 |
| EP | 2844771 A1 | 3/2015 |
| JP | 2010510557 A | 4/2010 |
| JP | 2012523645 A | 10/2012 |
| JP | 2015535681 A | 12/2015 |
| RU | 2014150655 A | 7/2016 |

(Continued)

OTHER PUBLICATIONS

Enoch M-A, Shen P-H, Xu K, Hodgkinson C, Goldman D. Using ancestry-informative markers to define populations and detect population stratification. Journal of Psychopharmacology 20(4): 19-26. (Year: 2006).*

(Continued)

*Primary Examiner* — Olivia M. Wise
*Assistant Examiner* — Robert J. Kallal
(74) *Attorney, Agent, or Firm* — Fletcher Yoder P.C.

(57) ABSTRACT

Presented herein are techniques for determining microsatellite instability. The techniques include generating a reference sample dataset representative of or mimicking a hypothetical matched sample for an individual sample of interest. The reference sample dataset may be generated from a set of reference normal samples that are not matched to the sample of interest. For samples of interest lacking a matched sample, the reference sample dataset may be used to determine microsatellite instability and to provide an indication of a presence, absence, or degree of microsatellite instability of the sample of interest. The reference sample dataset may be generated such that individual microsatellite regions associated with a high degree of variability between ethnic groups are filtered out, masked, or otherwise not considered.

14 Claims, 30 Drawing Sheets

(56) References Cited

FOREIGN PATENT DOCUMENTS

| WO | 2005/065814 | A1 | 7/2005 |
|---|---|---|---|
| WO | 2006/064199 | A1 | 6/2006 |
| WO | 2007/010251 | A1 | 1/2007 |
| WO | 2011/139901 | A1 | 11/2011 |
| WO | 2013052913 | A2 | 4/2013 |
| WO | 2013166517 | A1 | 11/2013 |
| WO | 2014204991 | A1 | 12/2014 |
| WO | 2015061359 | A1 | 4/2015 |
| WO | 2016/077553 | A1 | 5/2016 |
| WO | 2017112738 | A1 | 6/2017 |
| WO | 2018057770 | A1 | 3/2018 |

OTHER PUBLICATIONS

Bruhn N, Beinert T, Oehm C, Jandrig B, Petersen I, Chen XQ, Possinger K, Fleischhacker M. Detection of microsatellite alterations in the DNA isolated from tumor cells and from plasma DNA of patients with lung cancer. Annals of the New York Academy of Sciences 906 (1): 72-82. (Year: 2006).*

Eschbach E, Schoning S. Identification of high-resolution microsatellites without a priori knowledge of genotypes using a simple scoring approach. Methods in Ecology and Evolution 4: 1076-1082, (Year: 2013).*

Muñoz I, Henriques D, Johnston JS, Chávez-Galarza J, Kryger P, Pinto MA. 2015. Reduced SNP Panels for Genetic Identification and Introgression Analysis in the Dark Honey Bee (Apis mellifera mellifera). Plos One. 10(4): e0124365. doi:10.1371/journal.pone.0124365 (Year: 2015).*

Simons, Ccjm. A novel classification of colorectal tumors based on microsatellite instability, the CpG island methylator phenotype and chromosomal instability: implications for prognosis. Annals of Oncology 24: 2048-2056. (Year: 2013).*

Beutler, E. Hematologic differences between African-Americans and whites: the role of iron deficiency and alpha-thalassemia on hemoglobin levels and mean corpuscular volume. Blood 106(2): 740-745. (Year: 2005).*

Mlddha S. Reliable pan-cancer microsatellite instability assessment by using targeted next-generation sequencing data. JCO Precision Oncology 1: 1-17. (Year: 2017).*

Sonay TB. A survey of tandem repeat instabilities and associated gene expression changes in 35 colorectal cancers. BMC Genomics 16: 702, 11 pages. (Year: 2015).*

Portales-Casamar E. DNA methylation signature of human fetal alcohol spectrum disorder. Epigenetics and Chromatin 9(25): 1-20. (Year: 2016).*

Hechtman JF. Universal screening for microsatellite instability in colorectal cancer in the clinical genomics era: new recommendations, methods, and considerations. Familial Cancer 16: 525-529. (Year: 2017).*

Halperin RF. A method to reduce ancestry related germline false positives in tumor only somatic variant calling. BMC Medical Genomics 10(61): 1-17. (Year: 2017).*

Grasso C. Assessing Copy Number Alterations in Targeted, Amplicon-Based Next-Generation Sequencing Data. Journal of Molecular Diagnostics 17(1): 53-63. (Year: 2015).*

Cockroft, et al., "A single-molecule nanopore device detects DNA polymerase activity with single-nucleotide resolution", J. Am. Chem. Soc, 130(3), Jan. 23, 2008, 818-820.

Healy, Ken, "Nanopore-based single-molecule DNA analysis", Nanomed. 2(4), 2007, 459-481.

Korlach, et al., "Selective aluminum passivation for targeted immobilization of single DNA polymerase molecules in zero-mode waveguide nanostructures", PNAS, vol. 105 No. 4, 2008, 1176-1181.

Le, D., et al., "Mismatch repair deficiency predicts response of solid tumors to PD-1 blockade", Science 357(6349), Jul. 28, 2017, 409-413.

Levene, et al., "Zero-Mode Waveguides for Single-Molecule Analysis at high concentrations", Science 299, 2003, 682-686.

Liu, B., et al., "Computational methods for detecting copy number variations in cancer genome use next generation sequencing: principles and challenges", Oncotarger 2013; vol. 4; No. 44;, Nov. 19, 2013, 1868-1881.

Lundquist, et al., "Parallel confocal detection of single molecules in real time", Opt. Lett. 33(9), 2008, 1026-1028.

Niu, B., et al., "MSIsensor: Microsatellite instability detection using paired tumor-normal sequence data", Bioinformatics 30(7), Apr. 1, 2014, 1015-6.

Soni, et al., "Progress toward Ultrafast DNA Sequencing Using Solid-State Nanopores", Clin Chem, 53(11), 2007, 1996-2001.

Leo, A., et al., "A GC-Wave Correction Algorithm that Improves the Analytical Performance of aCGH", Journal of Molecular Diagnostics 14(6), Nov. 2012, 550-559.

PCT/US2018/061067, "International Search Report", Mar. 11, 2019, 1-4.

Umar, A., et al., "Revised Bethesda Guidelines for hereditary nonpolyposis colorectal cancer (Lynch syndrome) and microsatellite instability.", J. Natl Cancer Inst 96(4), Feb. 18, 2004, 261-8.

Janevski, A., et al., "Effective normalization for copy number variation detection from whole genome sequencing", BMC Genomics 13 Suppl 6(Suppl 6):S16. doi: 10.1186/1471-2164-13-S6-S16., Oct. 26, 2012, 1-11.

Kadalayil, L., et al., "Exome sequence read depth methods for identifying copy number changes", Briefings in Bioinformatics 16(3) https://doi.org/10.1093/bib/bbu027, Aug. 28, 2014, 380-392.

Peter Findeisen et al., "T25 Repeat in the 3' Untranslated Region of the CASP2 Gene: A Sensitive and Specific Marker for Microsatellite Instability in Colorectal Cancer", Priority Report, Cancer Res 2005; 65: (18), Sep. 15, 2005, pp. 8072-8078.

Yuchao Jiang et al., "CODEX: a normalization and copy number variation detection method for whole exome sequencing," Nucleic Acids Research, 43(6):e39 (Jan. 23, 2015), 12 pages.

Umar, A. et al.; "Revised Bethesda Guidelines for hereditary nonpolyposis colorectal cancer (Lynch syndrome) and microsatellite instability," J. Natl Cancer Inst. 96(4), Feb. 18, 2004, 261-268, 16 pages.

PCT/US2018/061067, "International Search Report," Mar. 13, 2019, 1-4.

International Search Report mailed Mar. 5, 2018 in International Application No. PCT/US2017/052766.

Yu Wang et al., "Identifying Human Genome-Wide CNV, LOH and UPD by Targeted Sequencing of Selected Regions", PLoS ONE, 10(7):e0132537, Apr. 28, 2015, 18 pages.

Second Office Action (with Translation), for MX/a/2019/003344 mailed Feb. 8, 2024, 16 pages.

Lonigro, R.J., et al., "Detection of somatic copy number alterations in cancer using targeted exome capture sequencing." Neoplasia, 13(11), pp. 1019-IN21. (Year: 2011).

Notice of Allowance for 10-2022-7017139 mailed Mar. 14, 2024, 5 pages.

O. Buhard 외, "Quasimonomorphic mononucleotide repeats for high-level microsatellite instability analysis", Dis Markers, 20(4-5):251-257. (2004.).

N. C. Campanella 외, "Optimization of a pentaplex panel for MSI analysis without control DNA in a Brazilian population: correlation with ancestry markers", Eur. J. Hum. Genet., 22(7):875-880. (2014.).

V. Deschoolmeester 외, "Detection of Microsatellite Instability in Colorectal Cancer ( 후략 )", J. Mol. Diagn., 10(2):154-159. (Mar. 2008).

O. Buhard 외, "HSP110 T17 simplifies and improves the microsatellite instability testing in patients with colorectal cancer", J. Med. Genet., 53(6):377-384. (Feb. 2016).

Bruhn, N. et al.; "Detection of microsatellite alterations in the DNA isolated from tumor cells and from plasma DNA of patients with lung cancer," Annals of the New York Academy of Sciences 906(1): 72-82. (Year: 2006).

Enoch, M-A, et al.; "Using ancestry-informative markers to define populations and detect population stratification," Journal of Psychopharmacology 20(4): 19-26. (Year: 2006).

(56) References Cited

OTHER PUBLICATIONS

Eschbach, E., et al.; "Identification of high resolution microsatellites without a prior knowledge of genotypes using a simple scoring approach," Methods in Ecology and Evolution 4: 1076-1082. (Year: 2013).

Munoz, I. et al.; "Reduced SNP Panels for Genetic Identification and Introgression Analysis in the Dark Honey Bee (*Apis mellifera mellifera*)," Plos One, 10(4): e0124365. doie:10.1371/journal.pone.0124365 (Year: 2015).

* cited by examiner

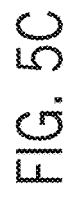
CTCTGCCAAAAAAAAAAAAAAAAAAAAAAGGCACAG
+ / − 1kb
CTCTGCCAAAAAAAAAAAAAAAAAAAAAAAAAAGGCACAG
FIG. 5A
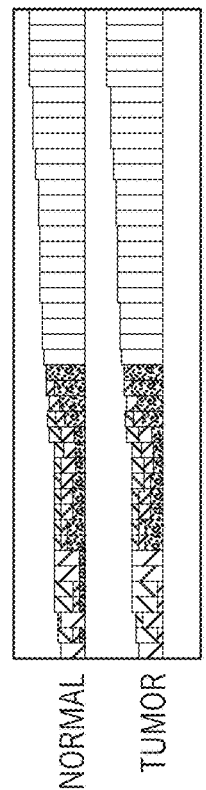
FIG. 5B
MSI-H SAMPLE
FIG. 5C
MSS SAMPLE
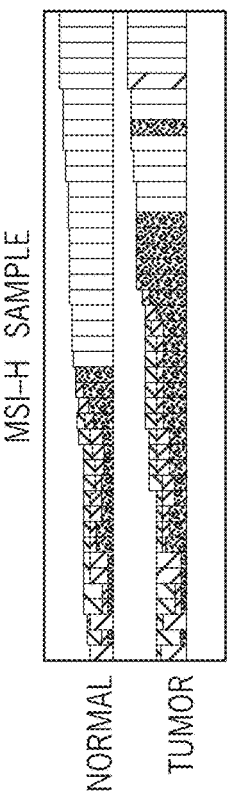
FIG. 5D
FIG. 5E

SYSTEMS AND METHODS FOR DETERMINING MICROSATELLITE INSTABILITY

CROSS-REFERENCE TO RELATED APPLICATIONS

The present application claims priority to and the benefit of U.S. Provisional Application No. 62/587,350, entitled "MICROSATELLITE INSTABILITY ASSESSMENT TECHNIQUES" FILED ON Nov. 16, 2017, the disclosure of which is incorporated by reference in its entirety herein for all purposes. The present application also claims priority to and the benefit of U.S. Provisional Application No. 62/652,151, entitled "MICROSATELLITE INSTABILITY ASSESSMENT TECHNIQUES WITH REDUCED BIAS" filed on Apr. 3, 2018, the disclosure of which is incorporated by reference in its entirety herein for all purposes.

BACKGROUND

The present disclosure relates generally to the field of data acquired from biological samples, such as sequence data. More particularly, the disclosure relates to techniques for assessing microsatellite instability via analysis of sequence data of biological samples that are independent of the presence of matched normal samples.

Genetic sequencing has become an increasingly important area of genetic research, promising future uses in diagnostic and other applications. Genetic sequencing data may be used to, among other applications, identify genetic mutations, modifications, variants, or polymorphisms that are associated with certain clinical outcomes. For example, certain genetic variants may be associated with a positive or negative disease outcome. Further, a subject's genetic changes over time or relative to a matched normal sample may provide clinically useful information. However, matched normal samples may not be available for every subject.

BRIEF DESCRIPTION

The present disclosure provides improved techniques for detecting and characterizing microsatellite instability using sequence data from samples of interest. As provided herein, microsatellite instability may refer to the presence of nucleic acid replication errors in microsatellite repeat regions, which are short tandem repeat sequences (e.g., one to six base pairs in length) that are present throughout the genome. While microsatellite repeats may occur in untranslated regions of the genome, microsatellites may also be present in coding regions. During DNA replication, cells with microsatellite instability fail to repair DNA replication errors, which in turn may result in frame-shift mutations in the replicated daughter strand.

The presence of microsatellite instability may be associated with certain clinical conditions. For example, microsatellite instability is a hallmark of hereditary cancer syndrome, called Lynch Syndrome, based on germline mutations of mismatch repair genes such as MLH1, PMS2, MSH2 and MSH6. Microsatellite instability status is typically assessed in clinical labs as an independent prognostic factor for favorable survival in cancer types such as colorectal and endometrial tumors. Further, certain treatment protocols or treatment options may be initiated to administer nivolumab or pembrolizumab for patients with solid tumors that have microsatellite instability high (MSI-H) designations or that are mismatch repair deficient (dMMR). Further, the treatment option may be to not administer pembrolizumab for patients with solid tumors that have microsatellite stable designations per a microsatellite instability score as determined herein. In another embodiment, the MSI typing (high, low, stable) may be used to determine whether a patient may benefit from adjuvant 5-fluorouracil (5-FU) chemotherapy. For colorectal cancer patients, adjuvant 5-fluorouracil (5-FU) chemotherapy may provide limited benefits in MSI-H patients. Therefore, an MSI-H designation may lead to cessation of or contraindication of adjuvant 5-fluorouracil (5-FU) chemotherapy. Such patients may instead be offered folinic acid, 5-FU and oxaliplatin. In another example, the MSI type of the patient may be used to determine if immunotherapy or chemotherapy is provided.

Accordingly, as provided herein, sequence data of samples of interest may be analyzed to determine a presence, absence, and/or degree of microsatellite instability in the sample of interest. Samples of interest with assessed microsatellite instability may be designated as MSI-H, microsatellite instability low (MSI-L), or microsatellite stable (MSS). The samples of interest may be tumor samples, and the microsatellite instability or stability designations may provide additional clinical information. As such, the present techniques may be used as part of or in conjunction with diagnosis, prognosis, and/or treatment protocols for cancer patients.

In certain embodiments, the present techniques permit assessment of samples of interest that do not have matched normal tissue samples. As provided herein, a reference sample dataset may be generated that is representative of a hypothetical matched normal sample for the sample of interest. The reference sample dataset may function as a universal matched normal sample. The reference sample dataset is generated from sequence data of the normal tissue of a plurality of individuals. When a tumor sample is tested, the appropriate reference sample dataset may be selected based on the tissue type, the sample origin, and other factors.

In certain embodiments, to generate a universal matched normal sample that may be applied to samples of interest independent of the ethnic background of the individual providing the sample, a reference sample dataset formed from samples of a multi-ethnic plurality of individuals (i.e., including individuals of a plurality of different ethnic backgrounds) may be assessed for microsatellite sites having relatively higher levels of variability between ethnic groups. Such sites may be eliminated or masked in the reference sample dataset, thus eliminating these highly variable sites from the analysis used to generate the overall microsatellite instability score representative of the sample of interest. In this manner, sites that are variable in normal samples due to variability between ethnic groups and not as a result of microsatellite instability do not introduce potentially erroneous results into the microsatellite instability score. Accordingly, the present techniques provide a more accurate microsatellite instability assessment for samples without a matched normal and independent of the ethnic background of the samples. In one example, the present techniques may be used to assess microsatellite instability for samples for which no ethnic background identification information is present. In another example, the reference sample dataset used as the hypothetical matched normal and that is generated with ethnically variable microsatellite regions filtered out of the dataset may be generally application to a wide variety of samples, thus eliminating additional processing steps or selection of an appropriate reference sample based on the ethnic background of the individual providing the sample of interest.

In an embodiment, a computer-implemented method of processing microsatellite instability is provided that includes the steps of acquiring reference sequence data from a plurality of reference biological samples corresponding to respective individuals, each reference biological sample being associated with one of a plurality of ethnic groups, the reference sequence data comprising nucleotide identity information for a plurality of microsatellite regions; analyzing, using a microprocessor, the reference sequence data to generate a distribution at each of the plurality of microsatellite regions for the plurality of reference biological samples; determining, using a microprocessor, ethnic group variability of the distribution at each of the plurality of microsatellite regions for the plurality of reference biological samples, the ethnic group variability being based on assessing reference sequence data associated with each ethnic group relative to other ethnic groups of the plurality of ethnic groups; determining ethnically unbiased microsatellite regions of the plurality of microsatellite regions having distributions with ethnic group variability below a threshold; generating, using a microprocessor, a reference sample dataset from the distribution at each of the determined ethnically unbiased microsatellite regions of the plurality of microsatellite regions; determining, using a microprocessor, microsatellite instability based on a comparison of sequence data from a sample of interest to the reference sample dataset, wherein the sample of interest is derived from a tumor sample of an individual without using a matched normal sample from the individual to the sample of interest; and outputting information on treatment options based on the determined microsatellite instability.

In another embodiment, a computer-implemented method is provided that includes the steps of acquiring, using a microprocessor, genomic reference sequence data from a plurality of reference biological samples corresponding to respective individuals; analyzing the reference sequence data to generate a distribution of sequences at each of a plurality of microsatellite regions; determining ethnic group variability of the distribution at each of the plurality of microsatellite regions for the plurality of reference biological samples, the ethnic group variability including genomic sequence differences; identifying ethnically biased microsatellite regions of the plurality of microsatellite regions based on the ethnic group variability at each of the plurality of microsatellite regions; and generating a reference sample dataset by removing or filtering the ethnically biased microsatellite regions from the reference sequence data of the plurality of reference biological samples.

In an embodiment, a method is provided that includes the steps of acquiring reference sequence data from a plurality of reference biological samples corresponding to respective individuals, and the reference sequence data comprising nucleotide identity information for a plurality of microsatellite regions; analyzing the reference sequence data to generate a distribution at each of the plurality of microsatellite regions; generating a reference sample dataset from the distribution at each of the plurality of microsatellite regions; and providing instructions to assess microsatellite instability based on a comparison of sequence data from a sample of interest to the reference sample dataset, wherein the sample of interest is derived from a tumor sample of an individual and wherein a matched normal sample from the individual to the sample of interest is not available.

In another embodiment, a system is provided that includes a processor; and a memory storing instructions that, when executed by the processor, cause the processor to access genomic sequence data of a sample of interest, wherein the sequence data comprises nucleotide identity information for a plurality of microsatellite regions; receive sample information related to the sample of interest; select an associated reference sample dataset from a plurality of reference sample datasets based on the sample information, wherein each of the reference sample datasets are generated from nucleotide identity information for the plurality of microsatellite regions and from a plurality of individuals; classify microsatellite instability for the sample of interest based on a comparison of the sequence data from the sample of interest to the associated reference sample dataset; and provide an indication representative of microsatellite instability for the sample of interest based on the classification.

In another embodiment, a system is provided that includes a processor; and a memory storing instructions that, when executed by the processor, cause the processor to access sequence data of a sample of interest, the sample of interest being derived from a tumor sample for which a matched normal sample is unavailable, wherein the sequence data comprises nucleotide identity information for a plurality of microsatellite regions; receive matched sample information for the sample of interest; and analyze the sequence data according to a first microsatellite analysis technique when the matched sample information is indicative of an absence of a matched normal tissue sample to the sample of interest to generate a first output indicative of microsatellite instability of the sample of interest; and analyze the sequence data according to a second microsatellite analysis technique when the matched sample information is indicative of a presence of a matched normal tissue sample to the sample of interest to generate a second output indicative of microsatellite instability of the sample of interest.

In another embodiment, a sequencing device is provided that is configured to acquire tumor sequence data of a tumor sample. The device includes a memory device including executable application instructions stored therein; and a processor configured to execute the application instructions stored in the memory device. The application instructions include instructions that cause the processor to: receive the tumor sequence data from sequencing device; identify a distribution of a plurality of microsatellite regions in the tumor sequence data; determine that the tumor sample is not associated with a matched normal sample; access reference sequence data; determine a microsatellite instability type of the tumor sample based on a comparison of the distribution of the tumor sample to a reference distribution of the reference sample dataset; and provide an indication of a treatment option based on a determination that the tumor sample is a microsatellite instability high type

DRAWINGS

Figure 12:
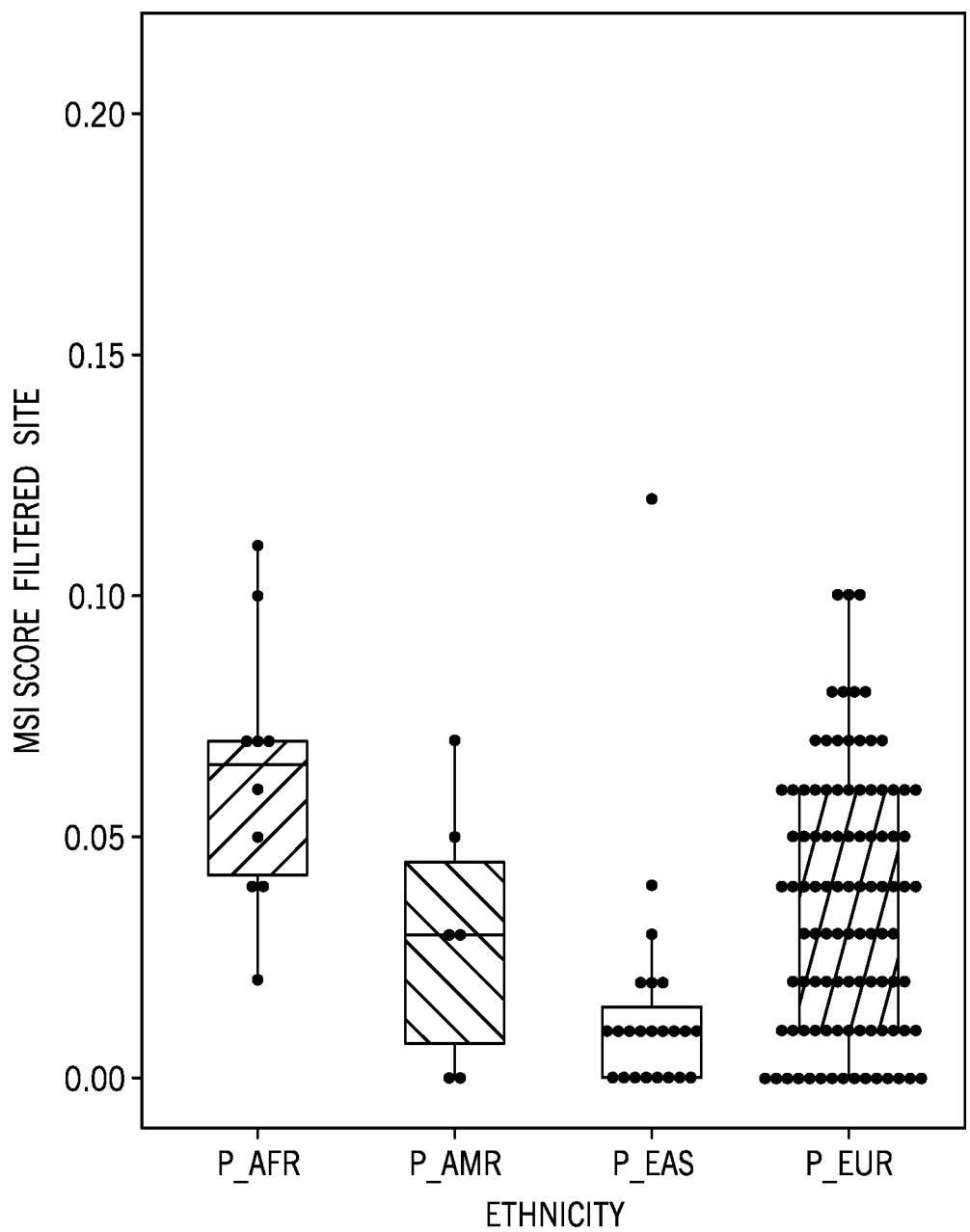
Figure 13:
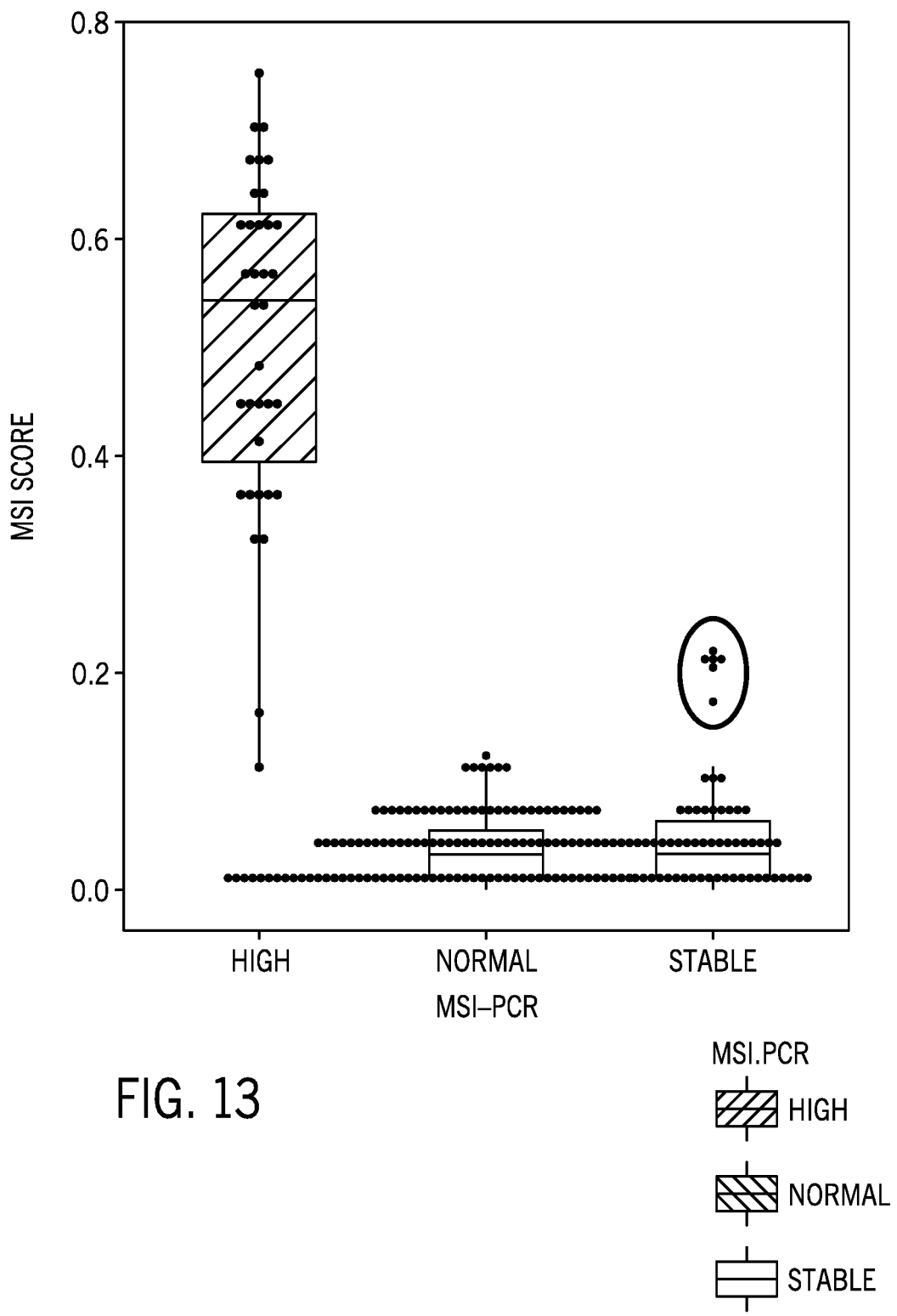
Figure 14:
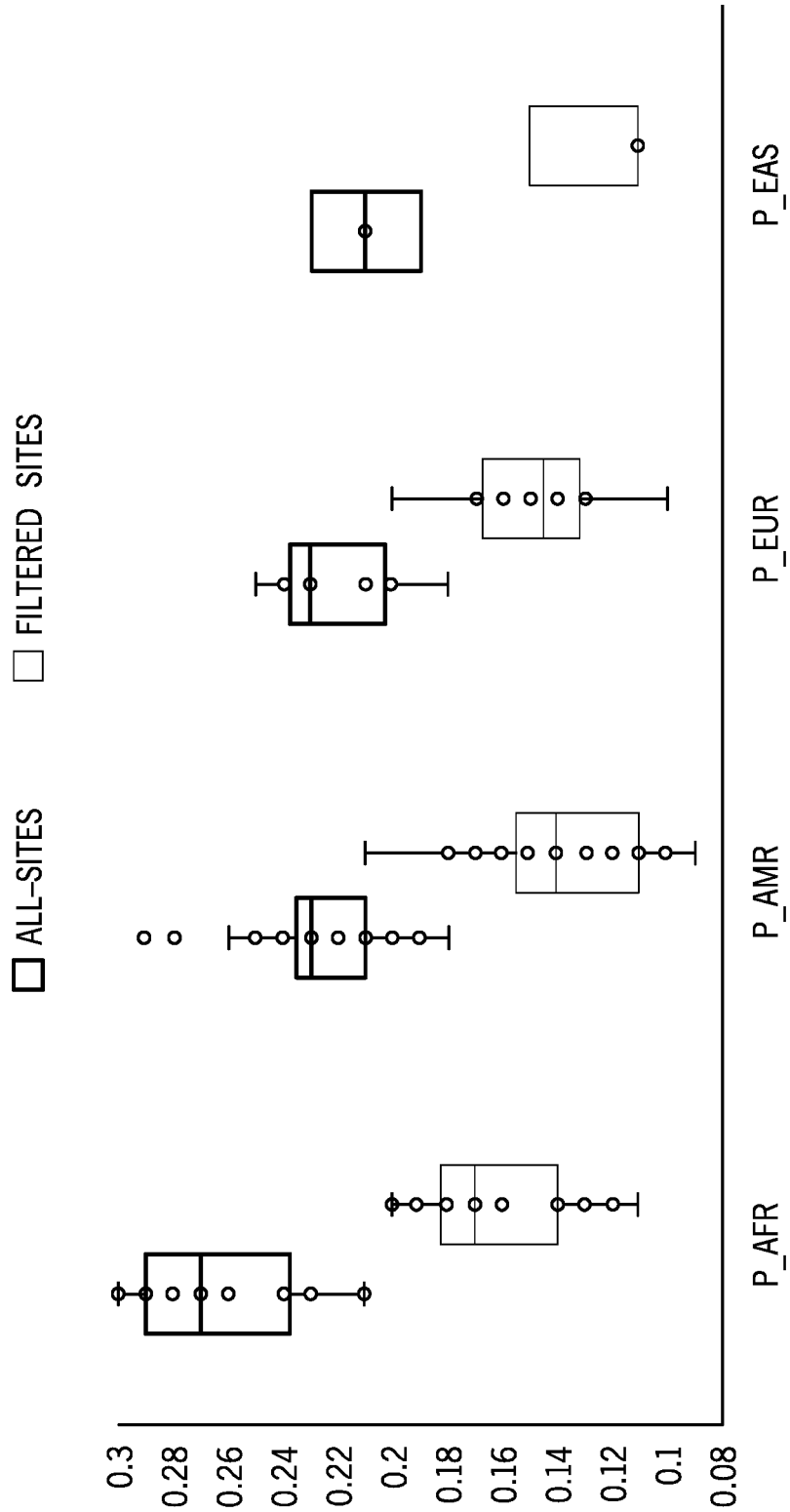
Figure 15:
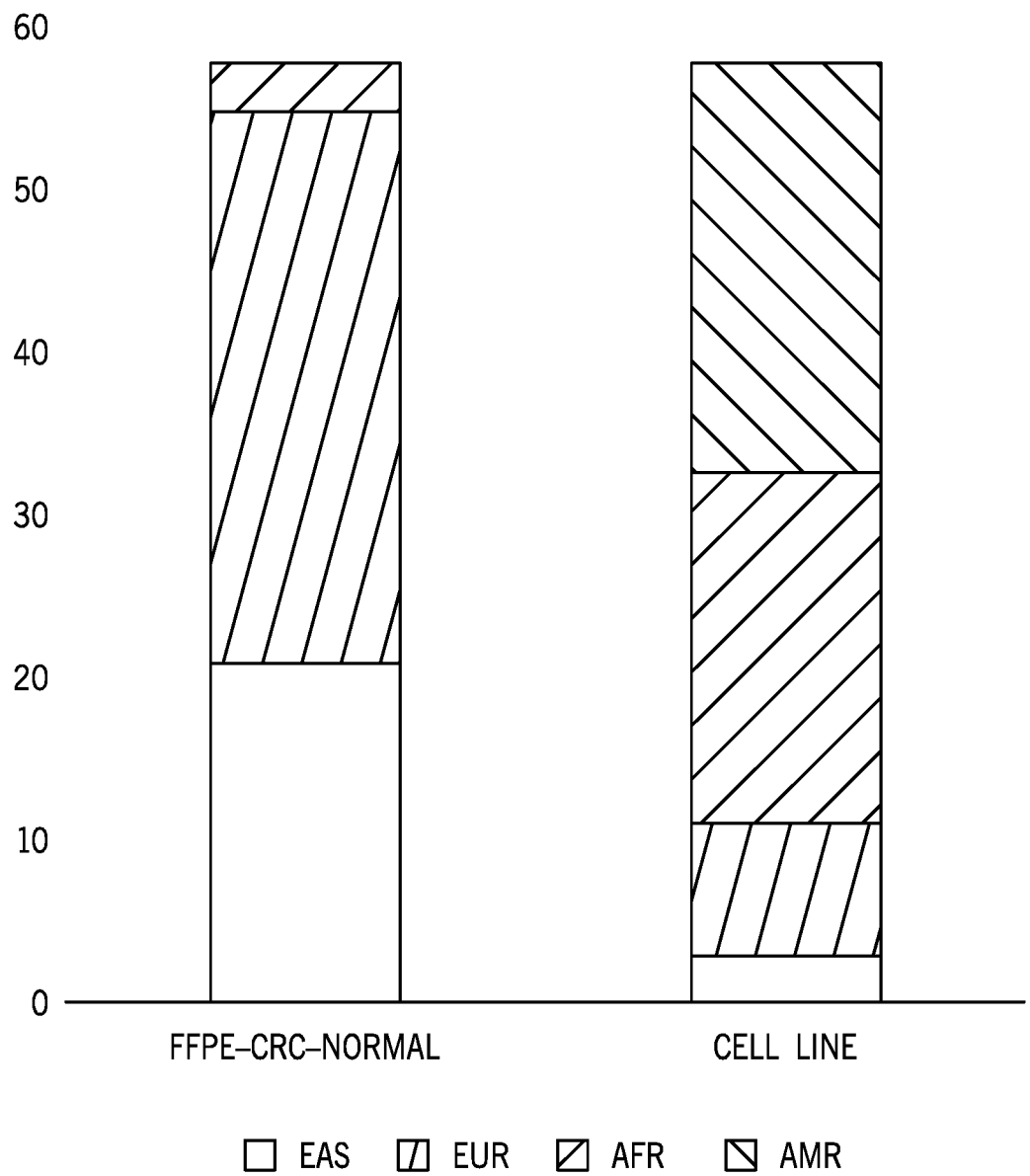
Figure 16B:
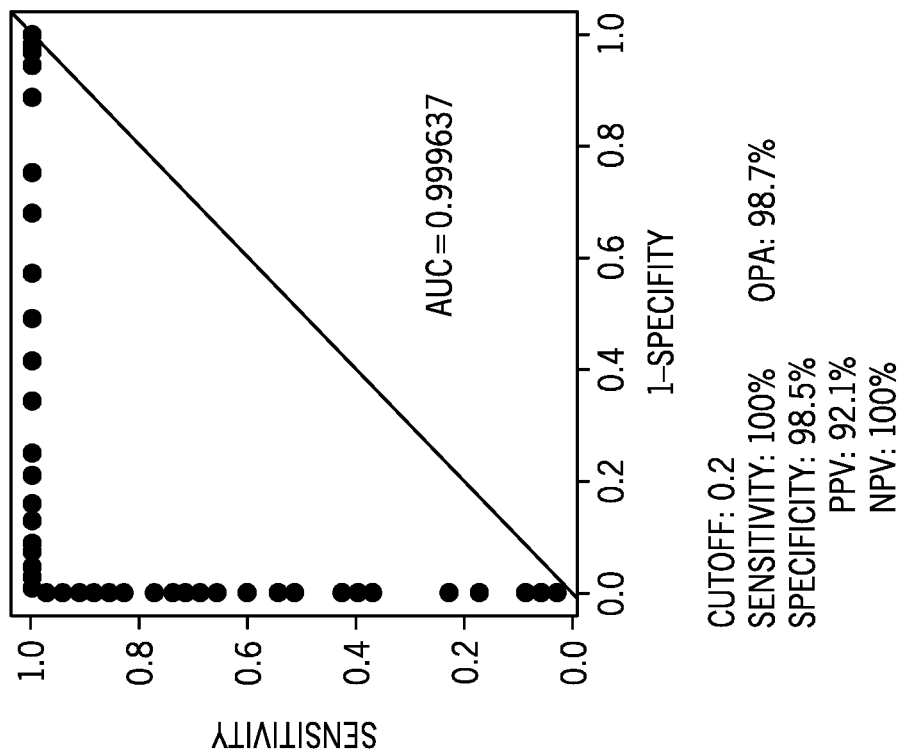
Figure 16A:
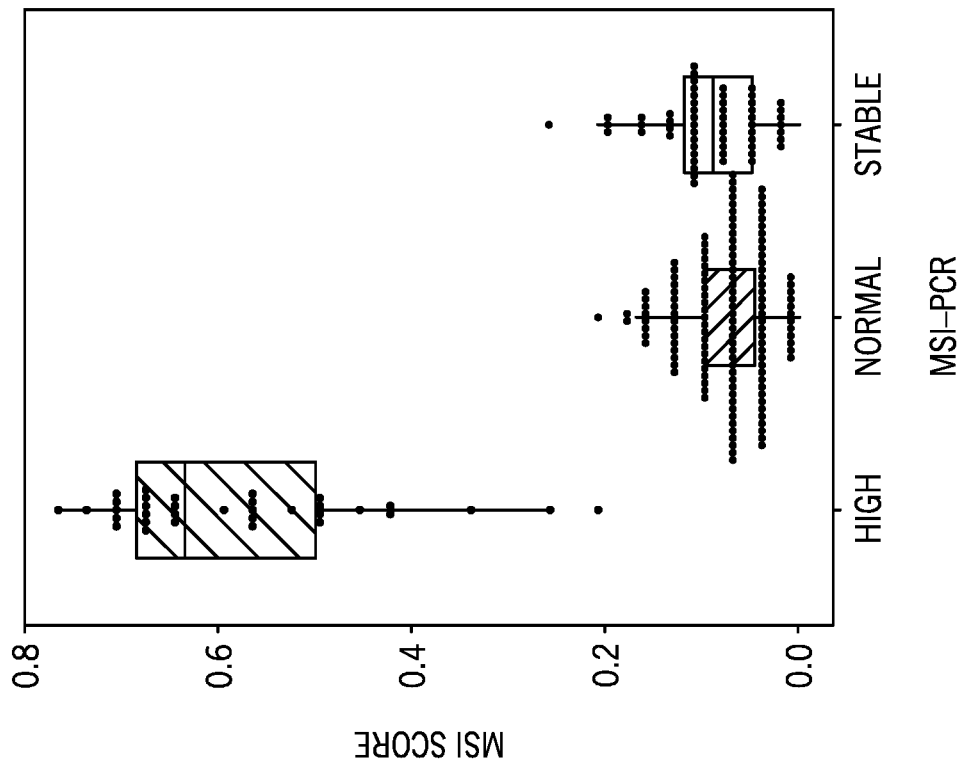
Figure 17:
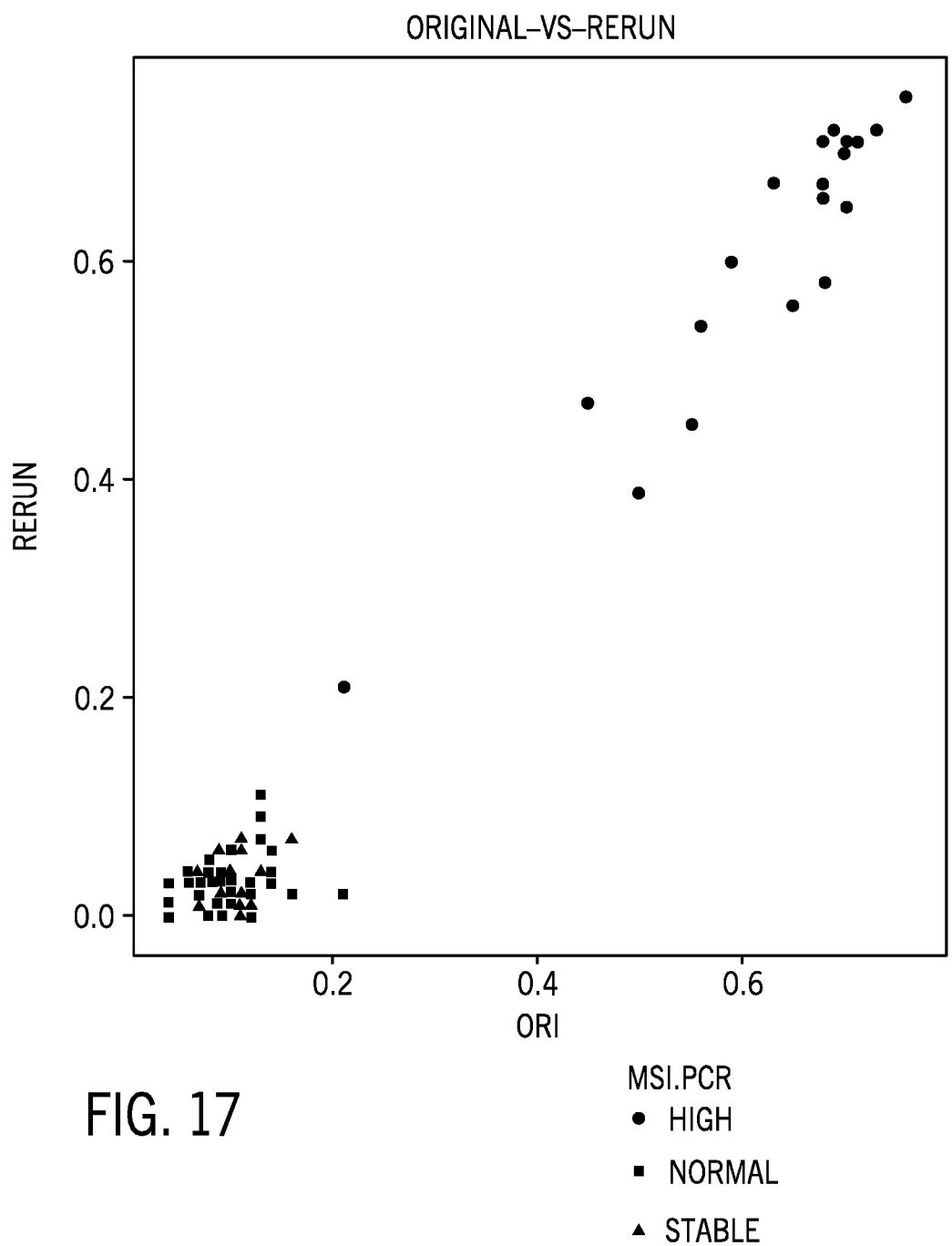
Figure 18:
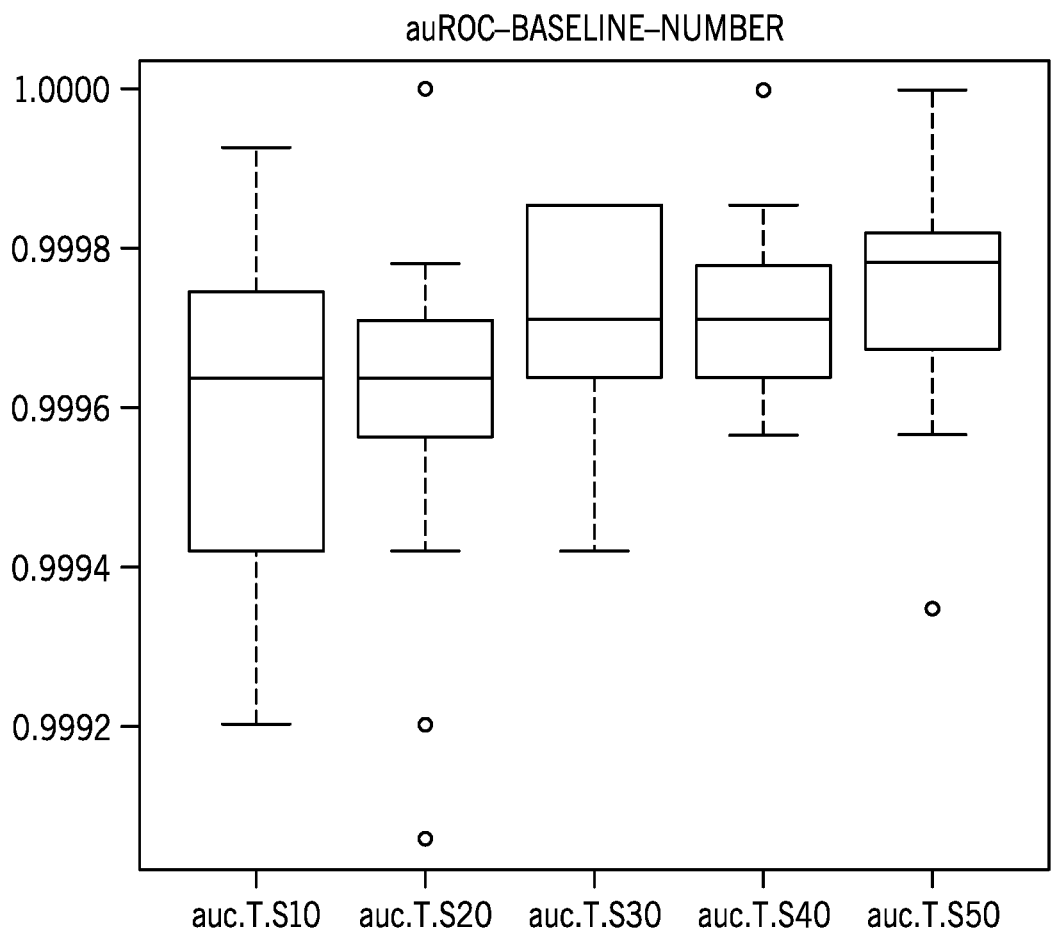
Figure 19:
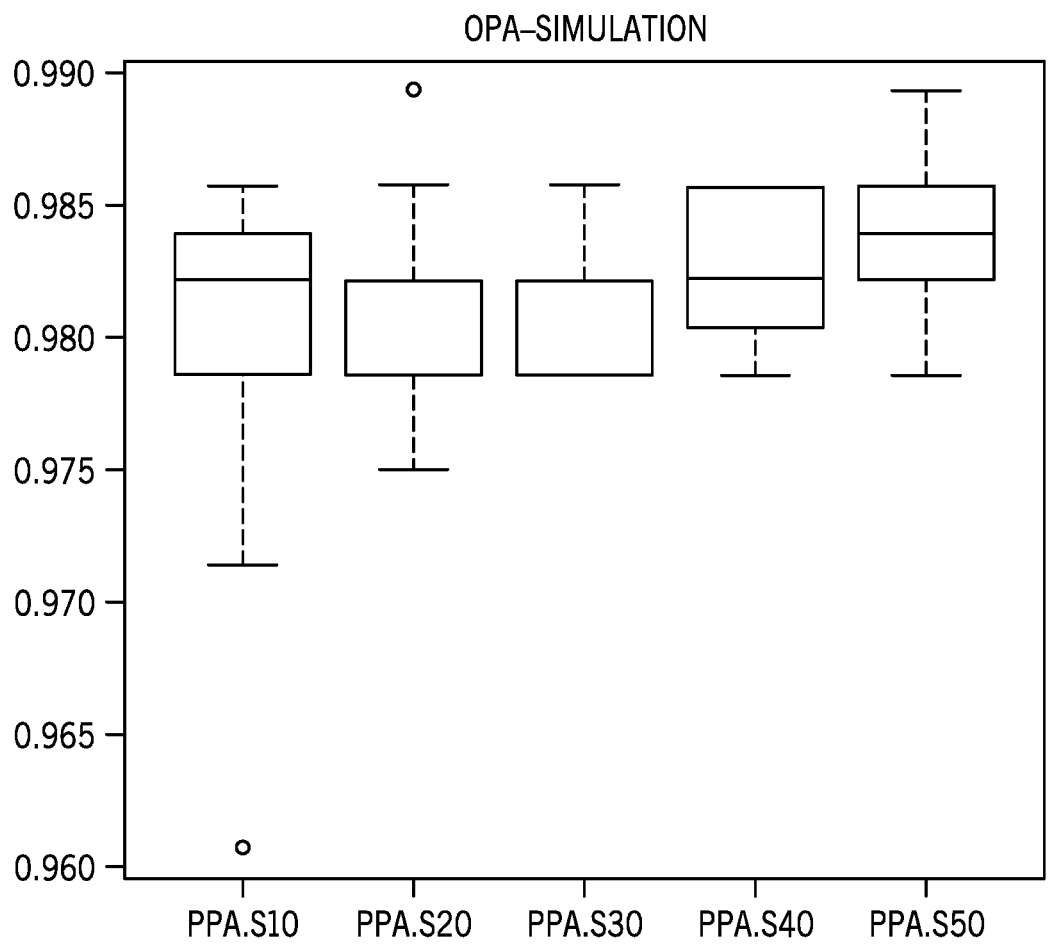
Figure 20:
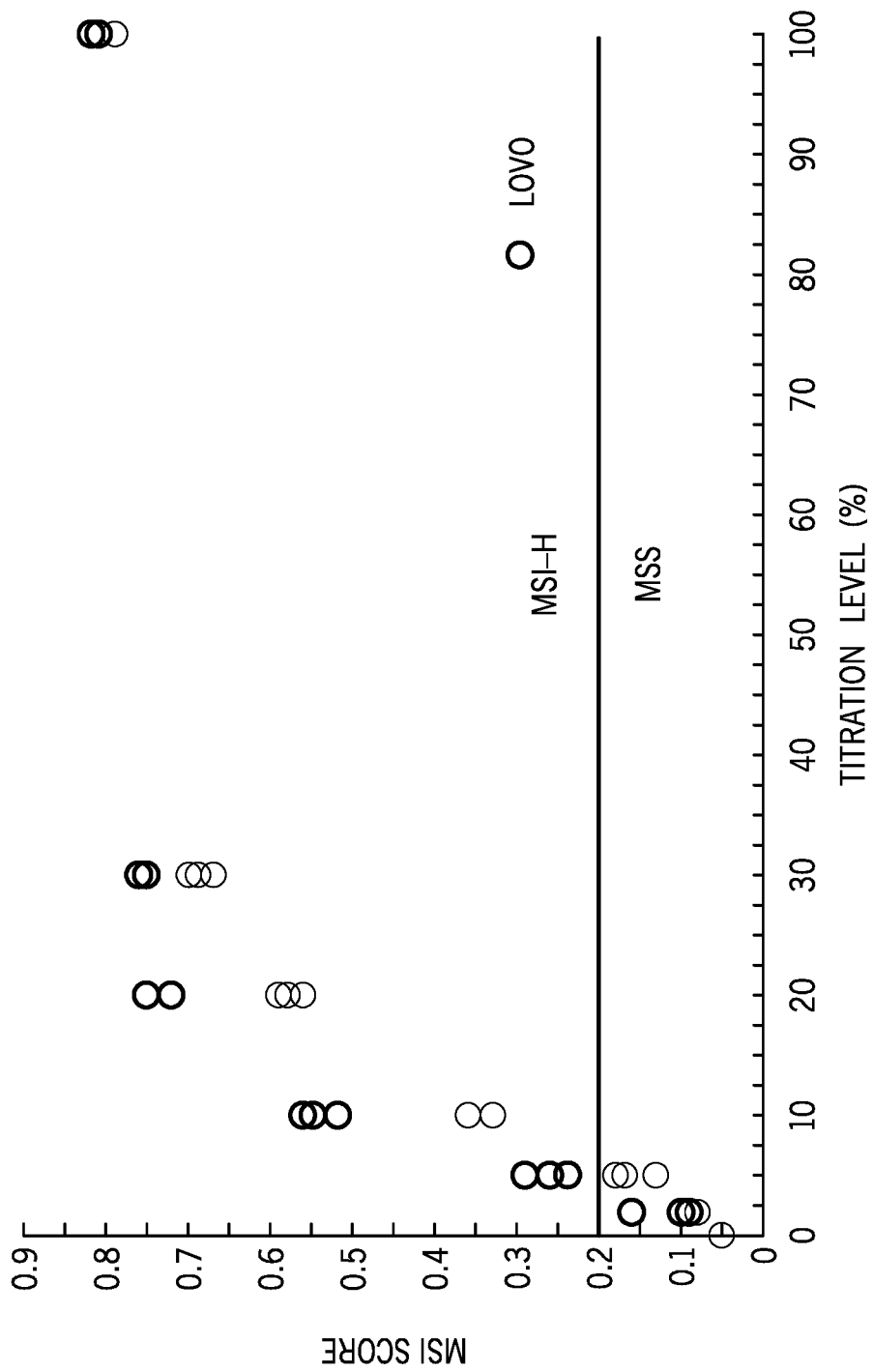
Figure 21:
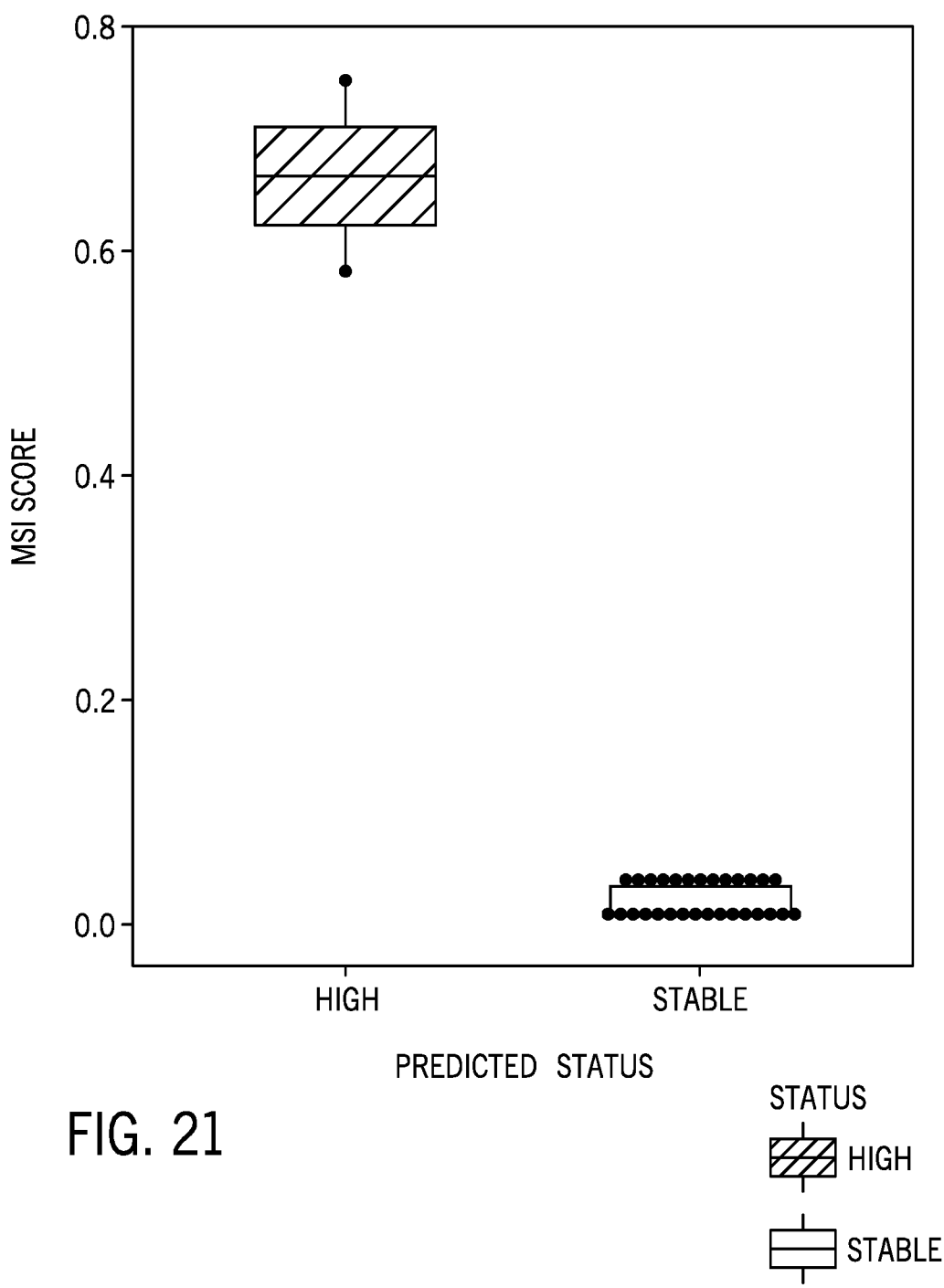
Figure 22:
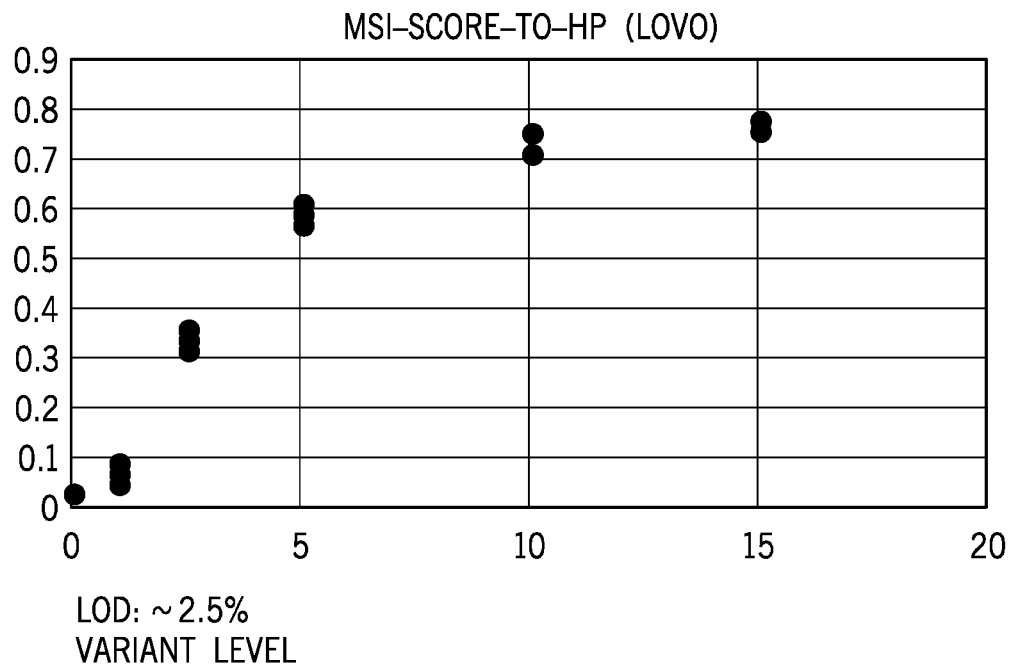
Figure 23:
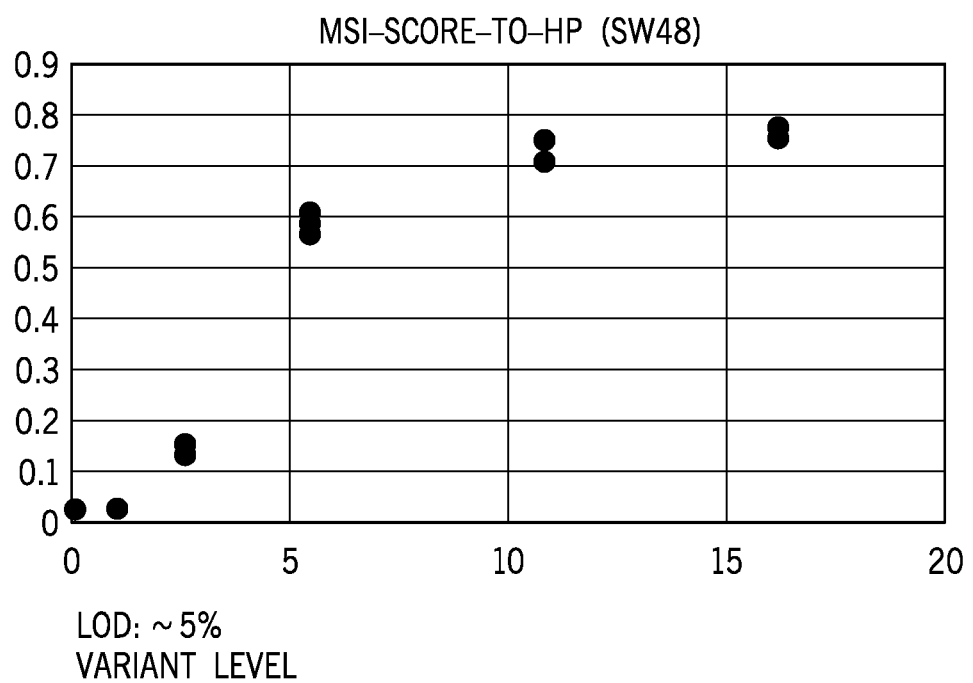
Figure 24:
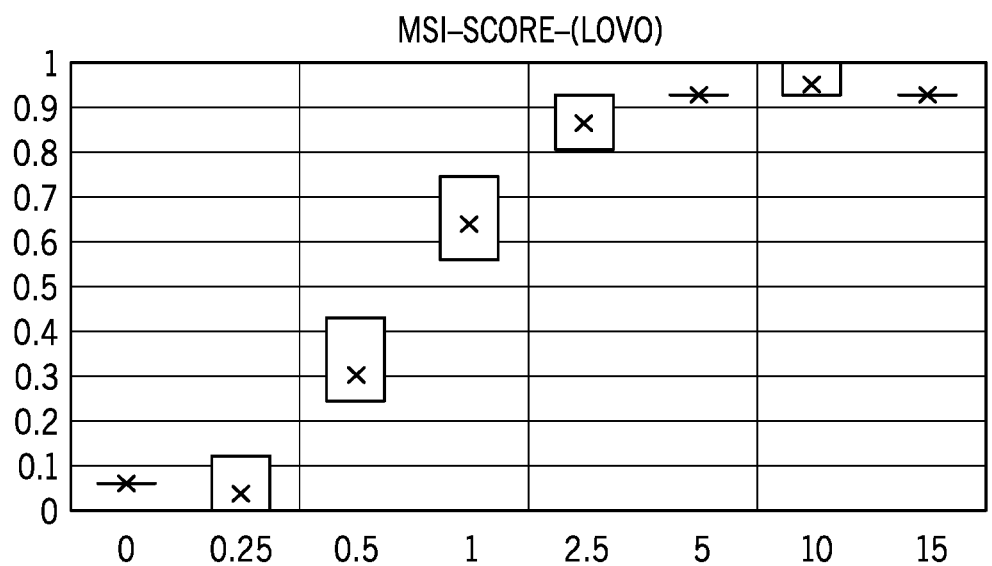
Figure 25:
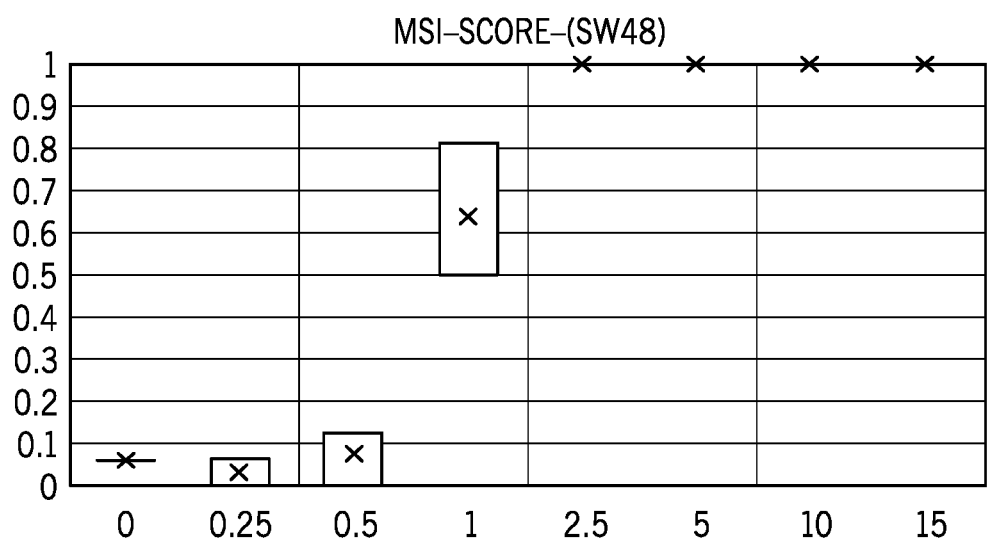

FIG. 12 is boxplot of a microsatellite instability score for 140 normal samples including samples from individuals associated with one of four different ethnic groups (African, South American, East Asian, and European) using the 58 sample normal colorectal cancer reference sample dataset with the identified microsatellite regions with relatively high ethnic variability filtered out of the reference sample dataset prior to the analysis;

FIG. 13 is boxplot of a microsatellite instability score of 232 tumor/normal samples from a variety of tissue types using the 58 sample normal colorectal cancer reference sample dataset post filtering with the red circle denoting potential false positives;

FIG. 14 is boxplot of a microsatellite instability score for normal samples associated with one of four different ethnic groups (African, South American, East Asian, and European) using 58 unmatched cell lines samples as the reference sample dataset pre and post filtering of the identified microsatellite regions with relatively high ethnic variability;

FIG. 15 is a comparison of the ethnic diversity of the unmatched cell lines samples reference dataset with the normal colorectal cancer reference sample dataset;

FIG. 16A is boxplot of a microsatellite instability score of 232 tumor/normal samples from a variety of tissue types using the unmatched cell lines samples as the reference sample dataset post filtering of the identified microsatellite regions with relatively high ethnic variability;

FIG. 16B shows the sensitivity and specificity of the results of FIG. 16A;

FIG. 17 is a comparison of an original and repeat run of 78 colorectal cancer samples;

FIG. 18 shows MSI score results correlation for reference sample datasets with varying numbers of samples;

FIG. 19 shows MSI score results correlation for reference sample datasets with varying numbers of samples;

FIG. 20 shows MSI scores for different titration levels of cell lines;

FIG. 21 is boxplot of a microsatellite instability score of 46 cell line samples including four MSI-H cell lines;

FIG. 22 shows limits of detection for titrated levels of Lovo cells using a microsatellite analysis technique according to embodiments of the disclosure;

FIG. 23 shows limits of detection for titrated levels of SW48 cells using a microsatellite analysis technique according to embodiments of the disclosure;

FIG. 24 shows limits of detection for titrated levels of Lovo cells using an improved and more stringent microsatellite analysis technique according to embodiments of the disclosure; and FIG. 25 shows limits of detection for titrated levels of SW48 cells using an improved and more stringent microsatellite analysis technique according to embodiments of the disclosure.

DETAILED DESCRIPTION

Assessing microsatellite instability of a tumor sample may provide information about potential prognosis or treatment options for a patient. However, in the clinical setting, matching normal tissues are not always available for samples of interest. For example, matched normal samples are often unavailable in retrospective studies when performing analysis with human material from clinical trials, pathology archives, and legacy bio-banks. In these cases, there is a need to identify and/or assess microsatellite instability from tumor tissues that do not have matched normal samples. Further, using a matched normal sample taken from the same individual as the biological sample presents certain challenges. For example, variation in sample collection (sample quality, selected tissue sites) may mean that reference sample is not truly representative of normal tissue. In addition, not all test samples have available matched tissue or matched tissue of sufficiently high quality for sequencing. Still further, samples of interest for a given assessment may be provided by individuals having a variety of ethnic backgrounds. Such variety is often desirable in studies to show effects of treatment protocols across the global population.

Microsatellite instability is typically detected by PCR (MSI-PCR) of certain microsatellites (e.g., using n=5 or 10 markers) followed by fragment length analysis through PCR and capillary electrophoresis to separate PCR amplicons. With MSI-PCR, each individual marker is evaluated by comparing how tumor markers shift from matched normal markers. That is, the instability is detected by a change in the characteristics of amplified alleles between the normal and the tumor sample. If more than 30% of microsatellites are shifted in the tumor sample compared to its matched normal sample, the tumor sample is categorized as MSI-high. If 10-20% of microsatellites are shifted, the tumor sample is categorized as MSI-low. If no microsatellite is shifted relative to the matched normal, the tumor sample is categorized as microsatellite stable.

In another example, immunohistochemical analysis (IHC) may be used to identify samples with microsatellite instability through identification of mismatch repair deficiencies. However mismatch repair IHC and microsatellite instability do not always correlate because other loss of function genes result in samples that exhibit the microsatellite instability phenotype (POLE). Samples that exhibit microsatellite instability due to other loss of function genes would not be identified when screening for mismatch repair genes using IHC. Further, mutations in the mismatch repair gene MSH6 tend to result in weaker or no microsatellite instability in the tumors. Such MSH6 cases may be missed by microsatellite instability testing but can be detectable by MSH6 mutation screening. In general, IHC is reliable in screening for mutations that result in truncation or degradation of the protein. IHC, however, cannot distinguish between mutant proteins commonly resulting from missense mutation and wild-type polypeptides. MSI-PCR and other microsatellite instability assessment techniques require comparison of tumor DNA with a matched normal sample. Further, the small number of assessed markers may impact test sensitivity.

Provided herein are techniques for determining microsatellite instability that use sequence data from a sample of interest. The techniques may include analyzing the sample relative to a reference sample dataset that functions as a hypothetical matched normal sample, even if no matched normal sample is available for the sample of interest. The reference sample dataset may be generated from sequence data from an unmatched normal cohort (i.e., sequence data from different individuals than the individual from whom the sample of interest was generated). The unmatched normal cohort may act as a universal matched normal for samples of interest. The sequence data may be assessed for any suitable number of microsatellite markers. The disclosed techniques provide a reference sample dataset that may be used without relying on the presence of a matched normal sample from the individual from whom the test sample is obtained. The disclosed techniques also provide a reference sample dataset that is screened for microsatellite regions having high variability between the unmatched cohort normal samples as a result of variability in ethnic background in the cohort. In this manner, the reference sample dataset serves as a hypothetical matched normal to any sample of interest, regardless of the ethnic background of the individual providing the sample of interest. In this manner, assessment of samples via identification of microsatellite instability in the samples may be expanded to a wider number of samples, e.g., samples without a matched normal, relative to other techniques. Further, by using a universal matched normal, the potential for user error via mismatching of tumor/normal samples in the analysis is reduced. That is, because the universal normal is the same sample for many different tumor samples, there is reduced possibility of misassignment of a tumor sample to its matched normal.

Accordingly, the disclosed techniques facilitate more accurate microsatellite assessment without using a matched sample. A universal or representative unmatched normal sample is generated using a set or cohort of unmatched reference biological samples. The representative unmatched normal sample information represents a virtual reference that may serve as a normal sample against which an individual tumor sample may be compared. The representative unmatched normal sample information represents a set of microsatellite regions having relatively low variability (e.g., lower than a pre-defined threshold) as a result of ethnic background variability in the cohort from which the unmatched normal sample information is generated.

Figure 1:
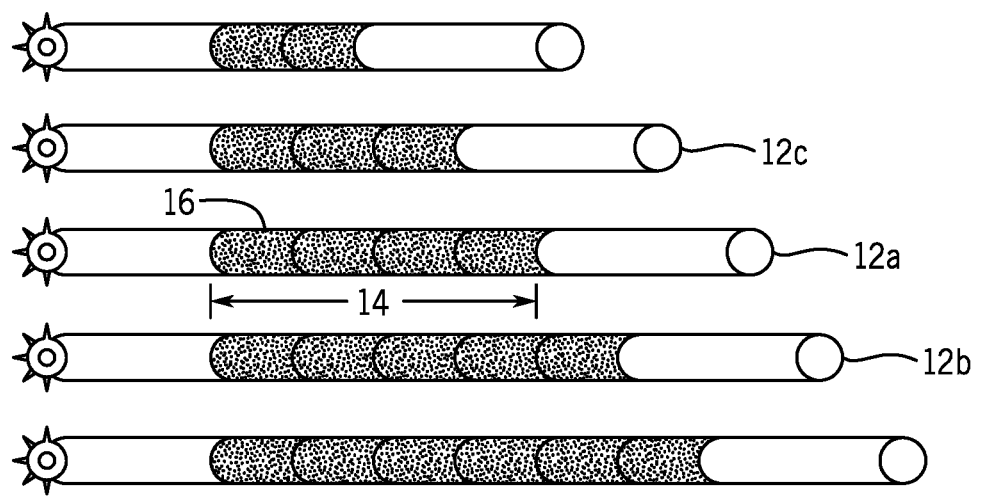
FIG. 1 is a schematic illustration of microsatellite instability in accordance with the present techniques.

To that end, FIG. 1 is a schematic illustration of microsatellite instability, represented as regions having different alleles caused by unrepaired replication errors. For example, as a result of polymerase slippage during replication, a parent strand (shown as strand 12a by way of example) may have a microsatellite region 14 having the sequence of N(n), where n is the number of repeat motifs 16, while daughter strand may have a sequence of N(n+1), e.g., as in the strand 12b, or N(n−1), e.g., as in the strand 12c, depending on the nature of the error, which results in alleles of different lengths at the microsatellite region. As provided herein, the assessment of microsatellite instability may determine whether there is divergence between allele distribution for samples of interest and allele distribution for matched normal, if available, or a representative unmatched normal sample. As shown, the distribution of strands 12 varies based on the variability of the microsatellite regions 14.

Figure 2:
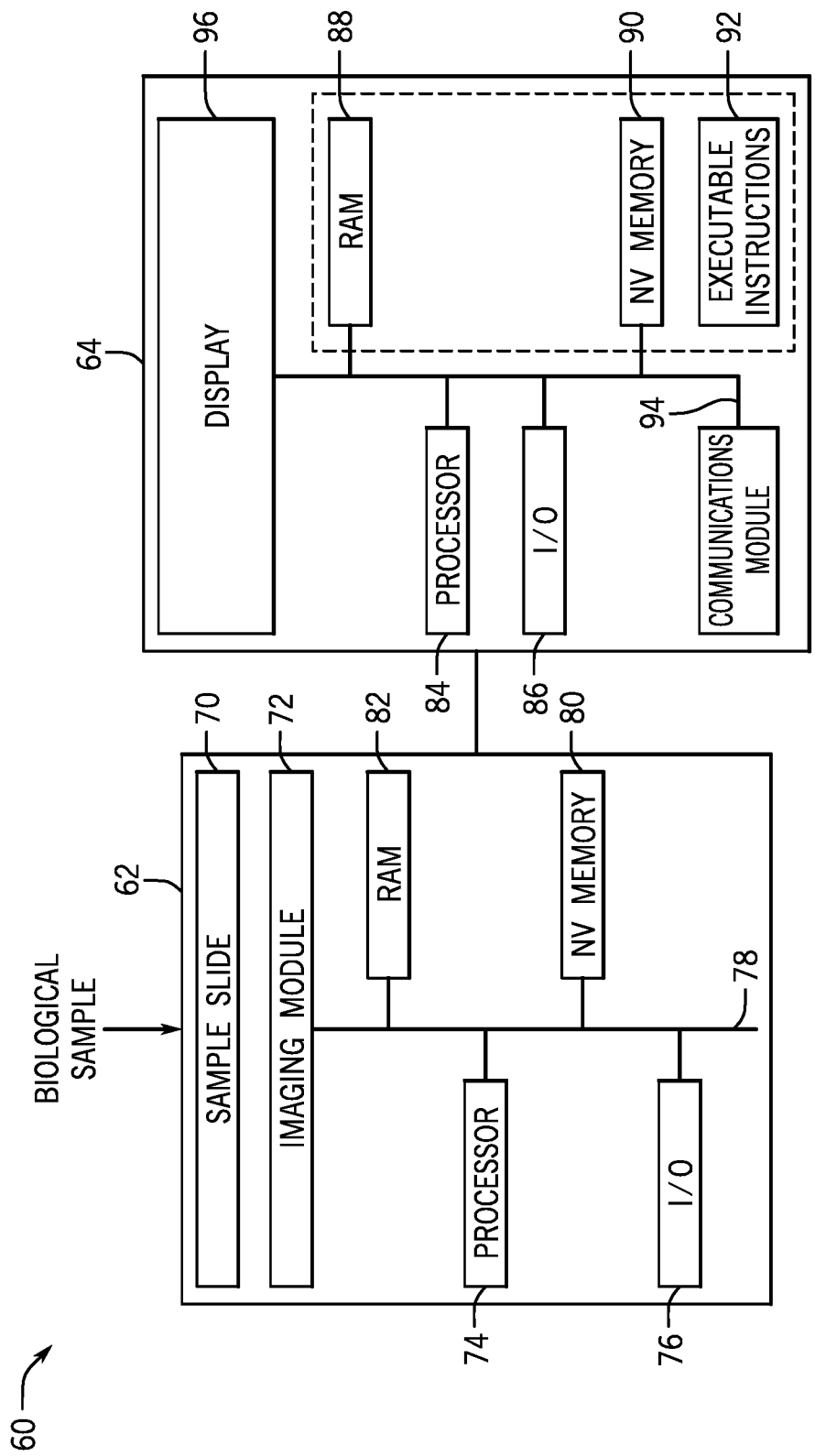
FIG. 2 is a block diagram of a sequencing device configured to acquire sequencing data in accordance with the present techniques.

FIG. 2 is a schematic diagram of a sequencing device 60 that may be used in conjunction with FIG. 1 for acquiring sequencing data (e.g., sample of interest sequencing data, unmatched cohort sequencing data) this is used for assessing microsatellite instability. The sequence device 60 may be implemented according to any sequencing technique, such as those incorporating sequencing-by-synthesis methods described in U.S. Patent Publication Nos. 2007/0166705; 2006/0188901; 2006/0240439; 2006/0281109; 2005/0100900; U.S. Pat. No. 7,057,026; WO 05/065814; WO 06/064199; WO 07/010,251, the disclosures of which are incorporated herein by reference in their entireties. Alternatively, sequencing by ligation techniques may be used in the sequencing device 60. Such techniques use DNA ligase to incorporate oligonucleotides and identify the incorporation of such oligonucleotides and are described in U.S. Pat. Nos. 6,969,488; 6,172,218; and 6,306,597; the disclosures of which are incorporated herein by reference in their entireties. Some embodiments can utilize nanopore sequencing, whereby target nucleic acid strands, or nucleotides exonucleolytically removed from target nucleic acids, pass through a nanopore. As the target nucleic acids or nucleotides pass through the nanopore, each type of base can be identified by measuring fluctuations in the electrical conductance of the pore (U.S. Pat. No. 7,001,792; Soni & Meller, Clin. Chem. 53, 1996-2001 (2007); Healy, Nanomed. 2, 459-481 (2007); and Cockroft, et al. J. Am. Chem. Soc. 130, 818-820 (2008), the disclosures of which are incorporated herein by reference in their entireties). Yet other embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary of/ThermoFisher) or sequencing methods and systems described in US 2009/0026082 A1; US 2009/0127589 A1; US 2010/0137143 A1; or US 2010/0282617 A1, each of which is incorporated herein by reference in its entirety. Particular embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides, or with zeromode waveguides as described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference in their entireties. Other suitable alternative techniques include, for example, fluorescent in situ sequencing (FISSEQ), and Massively Parallel Signature Sequencing (MPSS). In particular embodiments, the sequencing device 60 may be a HiSeq, MiSeq, or HiScanSQ from Illumina (La Jolla, CA).

In the depicted embodiment, the sequencing device 60 includes a separate sample processing device 62 and an associated analysis device 64. However, as noted, these may be implemented as a single device. Further, the analysis device 64 may be local to or networked with the sample processing device 62. In the depicted embodiment, the biological sample may be loaded into the sample processing device 62 as a sample slide 70 that is imaged to generate sequence data. For example, reagents that interact with the biological sample fluoresce at particular wavelengths in response to an excitation beam generated by an imaging module 72 and thereby return radiation for imaging. For instance, the fluorescent components may be generated by fluorescently tagged nucleic acids that hybridize to complementary molecules of the components or to fluorescently tagged nucleotides that are incorporated into an oligonucleotide using a polymerase. As will be appreciated by those skilled in the art, the wavelength at which the dyes of the sample are excited and the wavelength at which they fluoresce will depend upon the absorption and emission spectra of the specific dyes. Such returned radiation may propagate back through the directing optics. This retrobeam may generally be directed toward detection optics of the imaging module 72.

The imaging module detection optics may be based upon any suitable technology, and may be, for example, a charged coupled device (CCD) sensor that generates pixilated image data based upon photons impacting locations in the device. However, it will be understood that any of a variety of other detectors may also be used including, but not limited to, a detector array configured for time delay integration (TDI) operation, a complementary metal oxide semiconductor (CMOS) detector, an avalanche photodiode (APD) detector, a Geiger-mode photon counter, or any other suitable detector. TDI mode detection can be coupled with line scanning as described in U.S. Pat. No. 7,329,860, which is incorporated herein by reference. Other useful detectors are described, for example, in the references provided previously herein in the context of various nucleic acid sequencing methodologies.

The imaging module 72 may be under processor control, e.g., via a processor 74 (e.g., a microprocessor), and the sample receiving device 18 may also include I/O controls 76, an internal bus 78, non-volatile memory 80, RAM 82 and any other memory structure such that the memory is capable of storing executable instructions, and other suitable hardware components that may be similar to those described with regard to FIG. 2. Further, the associated computer 20 may also include a processor 84, I/O controls 86, a communications module 84, and a memory architecture including RAM 88 and non-volatile memory 90, such that the memory architecture is capable of storing executable instructions 92. The hardware components may be linked by an internal bus 94, which may also link to the display 96. In embodiments in which the sequencing device is implemented as an all-in-one device, certain redundant hardware elements may be eliminated.

Figure 3:
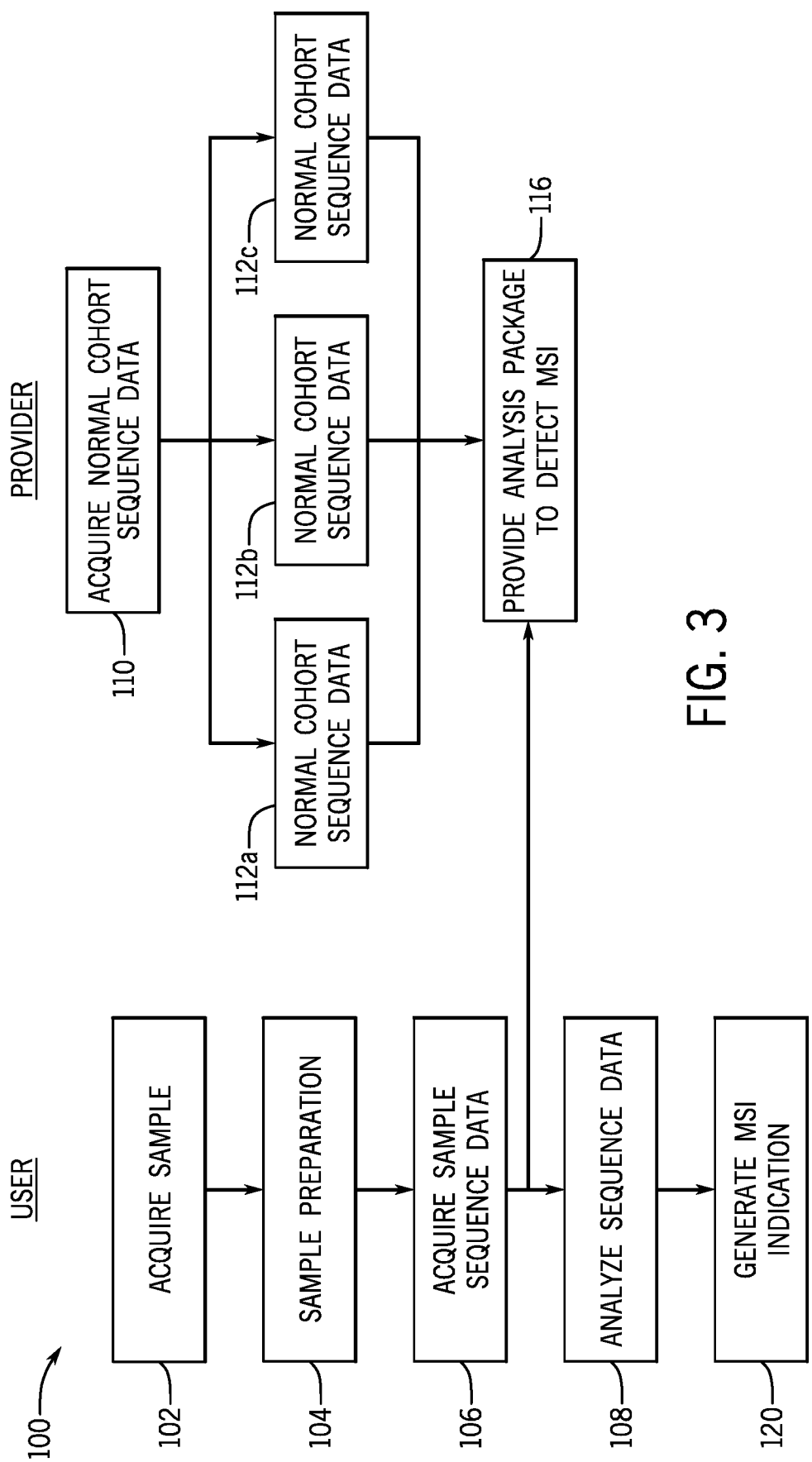
FIG. 3 is a flow diagram of methods of assessing microsatellite instability of a sample in accordance with the present techniques.

FIG. 3 is a flow diagram of a method 100 of assessing microsatellite instability. The steps of the method 100 may be performed by a user and/or a provider as shown. For example, a user may be an end user of the sequencing device, such as an owner of the sequencing device, a contractor of the sequencing device, a user of the sequencing device. The user may be a user interested in identifying microsatellite instability in one or more samples. The provider may be a provider of the universal matched normal reference sequence as provided herein. Further, in certain embodiments, the user and the provider may be the same entity. That is, the microsatellite assessment may be performed by the provider of the universal matched normal reference sequence.

At step 102, a sample of interest is acquired and sample preparation for sequencing occurs at step 104. Sample preparation may be based on sample type (e.g., liquid sample, solid sample, FFPE sample, plasma sample). Sequence data may be acquired at step 106 using a sequencing device 60 as provided herein. In other embodiments, previously acquired sequence data may be accessed. It should be understood that the biological sample sequencing data (i.e., the sample of interest, the representative unmatched normal samples, matched normal samples) as provided herein may be in the form of raw data, base call data providing nucleotide identities, or data that has gone through primary or secondary analysis (sequence alignment maps, binary alignment maps).

The analysis device may, via the display 96, provide a graphical user interface that facilitates user input of information related to sequencing reactions using the microsatellite instability assessment techniques as provided herein. For example, the user may provide input relating to a name or identification of each sample in the sequencing run, the sample origin (i.e., nucleic acids prepared from FFPE samples, fresh frozen samples, cell lines), a sequencing panel (i.e., a set of sequencing probes) used to acquire the sequence data, and the tissue type of the sample of interest. The user may also provide input related to whether a matched normal sample is available.

The present techniques facilitate detecting or assessment of microsatellite instability in biological samples (e.g., tumor samples) at step 108 without sequencing data from a matched normal sample. Accordingly, the method 100 acquires sequence data from a normal cohort at step 110. In certain embodiments, after generation and storage, the universal or representative normal sample sequence data, generated from a cohort of multiple samples, is used in the analysis of a plurality of samples of interest at different and/or subsequent time points. The user may access the stored files based on the cohort that most closely aligns with the sample of interest characteristics. To that end, multiple different normal cohort sequence data sets 112 may be acquired. Different normal cohort sequence data sets 112 may represent different sample types (nucleic acids prepared from normal FFPE samples, fresh frozen samples, cell lines), sequencing panels, tissue types, etc. The normal cohort sequence data 112 may be acquired from a suitable size cohort (at least 10 individuals, at least 20 individuals, at least 50 individuals) to provide a sufficient number of usable sequences for each microsatellite region examined. The individuals (or samples representative of different individuals) in each cohort may provide samples from normal cells or tissues that may be used to acquire the normal cohort sequence data (i.e., representative normal sample sequence data). The cohorts represent individuals that are not matched to the samples of interest, i.e., are different individuals.

In one embodiment, the representative unmatched normal sample sequence data, once generated, is fixed for a particular sample preparation technique. That is, the representative unmatched normal sample sequence data is associated with the type of samples from which the data was generated. Different representative unmatched normal sample sequence data sets may be generate for FFPE samples, cell lines, fresh frozen, etc. Further, the representative unmatched normal sample sequence data sets may be stored by the provider and sent to the user as part of an analysis package at step 116. The analysis package may also be capable of receiving updates from a remote server if the microsatellite instability analysis is refined by the provider.

In one embodiment, the normal cohort sequence data may include sequence data from a plurality of individuals. Each individual sequence may be assessed according to certain quality metrics (e.g. depth of sequencing) at each individual microsatellite region. For example, the sequence data of each individual sequence may only be used when there are at least a predetermined number (e.g., 20) sequencing reads at the individual microsatellite region. Accordingly, each individual sequence may pass at a subset of the microsatellite regions and fail for others, depending on the available sequencing depth. The passing regions are used for further analysis, while the failing regions are masked or not used. After quality assessment, the individual sequences of the cohort may be pooled to generate a distribution at each microsatellite region. The distribution of the pooled normal cohort serves as a reference sample dataset that represents a hypothetical matched normal sample.

The analysis maybe used to generate a microsatellite instability score at step 120. The microsatellite instability score may be based on a comparison of a distance (i.e., a statistical distance, a Jensen-Shannon distance) between a distribution at each microsatellite region between the sample of interest and the reference sample dataset. In one embodiment, a microsatellite instability score is based on a number of microsatellite regions having a distance above a threshold, where a larger distance is indicative of greater divergence from the reference sample dataset and being associated with a positive score, relative to a total number of microsatellite regions. Samples having a percentage greater than a predetermined number (e.g., 5%) having a positive score may be classified as having microsatellite instability while samples having a percentage lower than the predetermined number may be classified as microsatellite stable. Further, microsatellite instability may be designated as high or low based on the percentage.

The microsatellite instability assessment may be provided to a clinician as an input for determining a treatment protocol. In recent years, immune checkpoint inhibitors have shown great promise in treating various cancer types; however, only a fraction of patients respond to this type of immunotherapy. PD-L1 protein expression measured by quantitative immunohistochemistry (IHC) is an FDA approved companion diagnostic or complementary assay for some immune checkpoint inhibitors. Pembrolizumab (KEYTRUDA, Merck & Co.) may be provided to patients with solid tumors that have microsatellite instability high (MSI-H) or mismatch repair deficient (dMMR).

Figure 4:
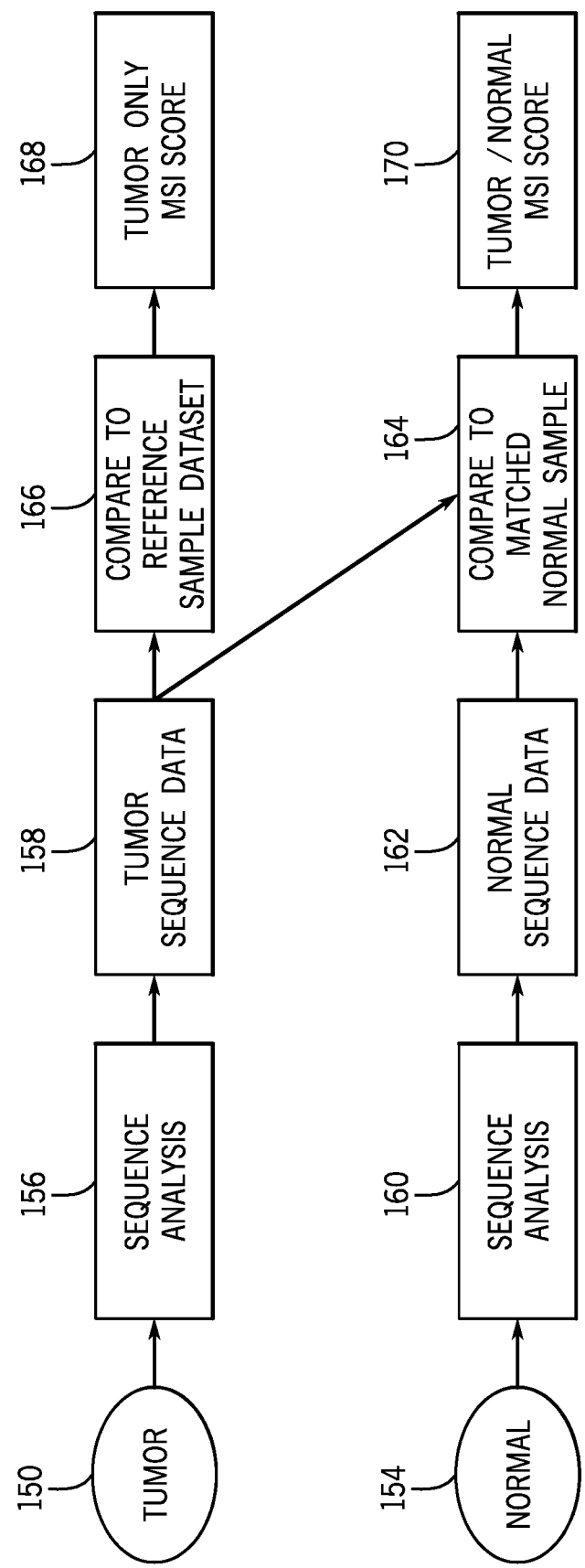
FIG. 4 is a flow diagram of a workflow for assessing microsatellite instability in matched or unmatched samples of interest in accordance with the present techniques.

FIG. 4 shows an example workflow for a sample of interest for an example tumor sample 150. If a matched normal sample 154 is available, the workflow proceeds to sequence analysis 156 of the tumor sample sequence data 158 and sequence analysis 160 of the normal sample sequence data 162. The sequence data may be in the form of BAM files, base call data, image data, etc. The sequence analysis may be via a microsatellite instability analysis technique in which the matched normal sample data is used as a basis for comparison (block 164). If no matched normal sample is available, the workflow proceeds to analysis via the microsatellite instability analysis technique as provided herein using the reference sample dataset from the appropriate unmatched normal cohort (block 166). Both techniques yield a microsatellite instability score, either a tumor only microsatellite instability score 168 or a tumor/normal microsatellite instability score 170. Further, for matched samples, the sample of interest may nonetheless be fed into the unmatched analysis and the results compared to the matched analysis for quality purposes.

In a specific embodiment, a sequencing panel was provided covering 170 genes associated with solid tumors. Designed to capture mutational changes, including single nucleotide variants, indels, amplifications, splice variants and fusions, the panel was designed to target both DNA and RNA variants from the same FFPE tumor sample in a single sequencing run. The performance of the panel to assess 103 microsatellite loci was evaluated using 53 colon cancer samples (28 MSI-H and 25 MSS as determined by MSI-PCR) and showed that the panel achieved 100% concordance for microsatellite instability status with matched tumor/normal pairs. Additionally the microsatellite instability analysis may be used for unmatched tumor sample only achieving 98% concordance with MSI-PCR. Furthermore, MSI-H samples had significantly higher tumor mutational burden compared to MSS samples in this cohort of colon samples. In summary, a microsatellite targeted panel may accurately determine microsatellite instability status from FFPE tumor samples. FIGS. 5, 6, and 7A-E show results from the experiments.

Figure 5A:
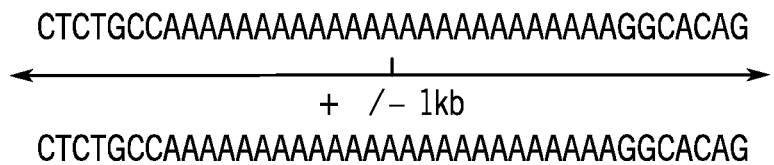
FIG. 5A is a schematic diagram of an example of a sequence read mapped to the microsatellite regions extracted from sequence data of colorectal tumor tissue and matched normal samples.
Figure 5B:
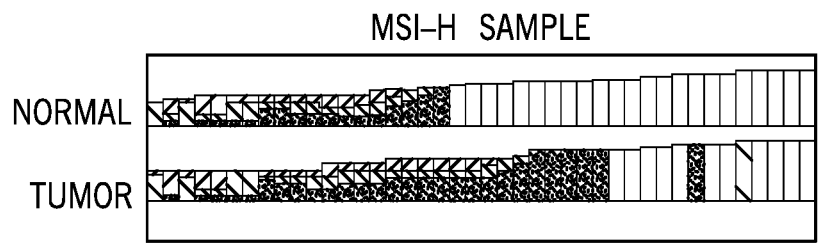
FIG. 5B shows for mapped reads of a microsatellite instability high (MSI-H) sample for both tumor and normal samples in a MSI-H sample.
Figure 5C:
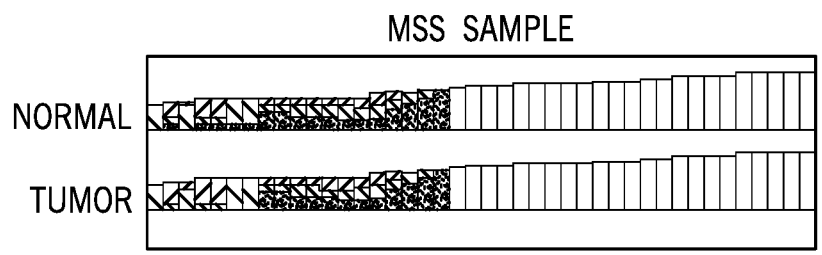
FIG. 5C shows mapped reads of a microsatellite stable (MSS) sample for both tumor and normal samples in the MSS sample.
Figure 5D:
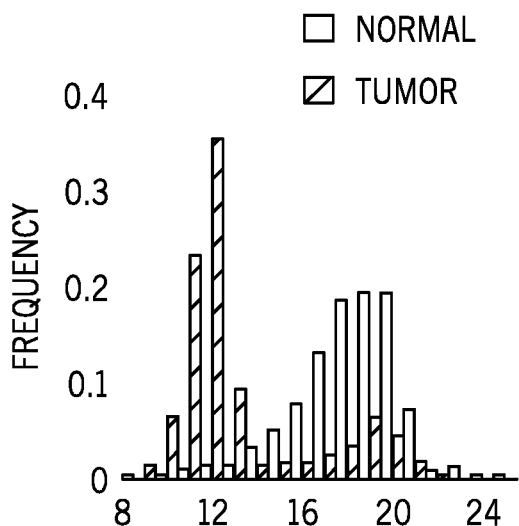
FIG. 5D shows repeat unit length distributions for both tumor and normal samples in the MSI-H sample of FIG. 5B.
Figure 5E:
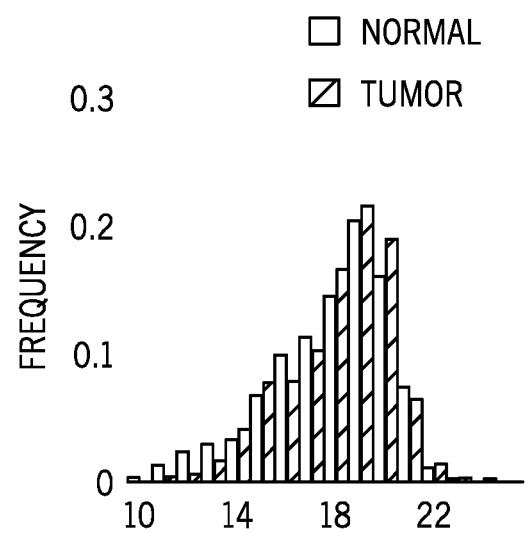
FIG. 5E shows repeat unit length distributions for both tumor and normal samples in the MSS sample of FIG. 5C.
Figure 6:
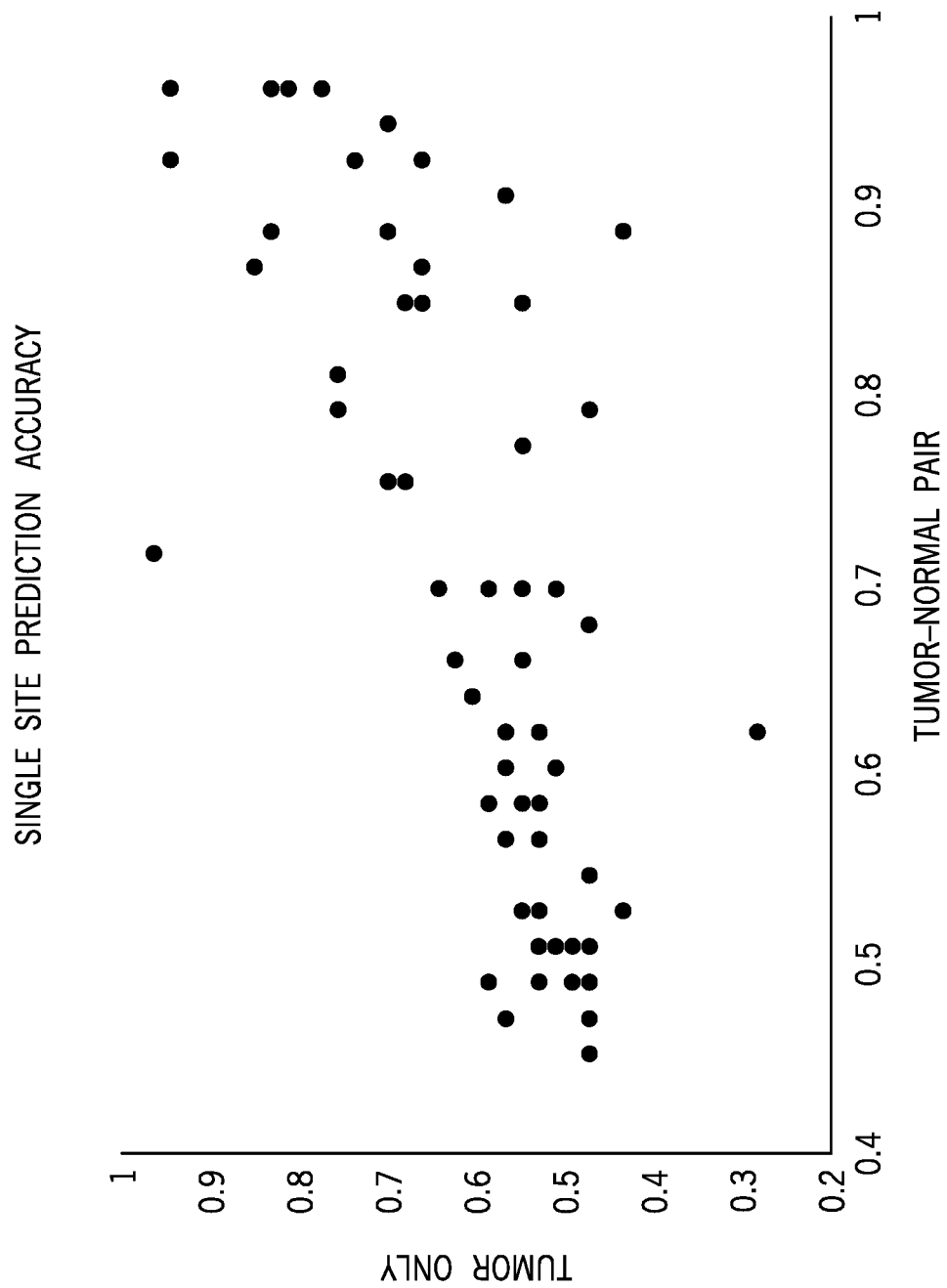
FIG. 6 shows prediction accuracy for single microsatellite sites for tumor only samples (y-axis) and tumor/normal pairs (x-axis)

For each microsatellite locus, flanking sequences of microsatellite repeats were anchored to determine the number of repeat units supported by reads mapped to the region. Subsequently the distribution of the repeat unit lengths determines the microsatellite instability status of each site. The final microsatellite instability score was calculated with number of unstable microsatellite sites divided by number of total sites evaluated. FIG. 5A shows reads mapped to the microsatellite regions that are extracted from a binary alignment map file. FIG. 5B shows for mapped reads of a microsatellite instability high (MSI-H) sample and FIG. 5D shows repeat unit length distributions for both tumor and normal samples in a MSI-H sample. FIG. 5C shows mapped reads of a microsatellite stable (MSS) sample and FIG. 5E shows repeat unit length distributions for both tumor and normal samples in the MSS sample. FIG. 6 shows single microsatellite region predictive value for each of the 103 sites of the sequencing panel. Single sites were less accurate relative to the full panel. As provided herein, the number of microsatellite sites or microsatellite regions used in the present techniques to generate a microsatellite instability score may be 1 or more, 5 or more, 50 or more, or 100 or more. In certain embodiments, the present techniques may analyze 1-20, 5-20, 5-50, 10-20, 10-50, or 50-100 microsatellite sites in the analysis to generate a microsatellite instability score.

As provided, the Jensen-Shannon Distance between the sample of interest to the reference sample dataset was determined. The reference Jensen-Shannon Distance, d1, was calculated for all pairwise combinations of reference samples (BL_n, n=1 . . . N) as follows:

$$BL\_n1 = Pr[X=x]$$

$$BL\_n2 = Pr[X=x]$$

$$JS1 = 0.5*(\text{sum}(BL\_n1*\log(BL\_n1/m1)) + \text{sum}(BL\_n1*\log(BL\_n1/m1)))$$

$$m1 = 0.5*(BL\_n1 + BL\_n2)$$

$$d1 = \text{sqrt}(JS1)$$

The test Jensen-Shannon Distance, d2, was calculated between the sample of interest (T) and each sample of the reference dataset as follows:

$$BL\_n = Pr[X=x]$$

$$T = Pr[X=x]$$

$$JS2 = 0.5*(\text{sum}(BL\_n*\log(BL\_n/m2)) + \text{sum}(T*\log(T/m2)))$$

$$m2 = 0.5*(BL1 + T)$$

$$d2 = \text{sqrt}(JS2)$$

Comparison between two Jensen-Shannon Distance distributions is performed via a one-sided t-test to establish d1<d2, with FDR<0.05 and d2−d1>0.1.

Figure 7A:
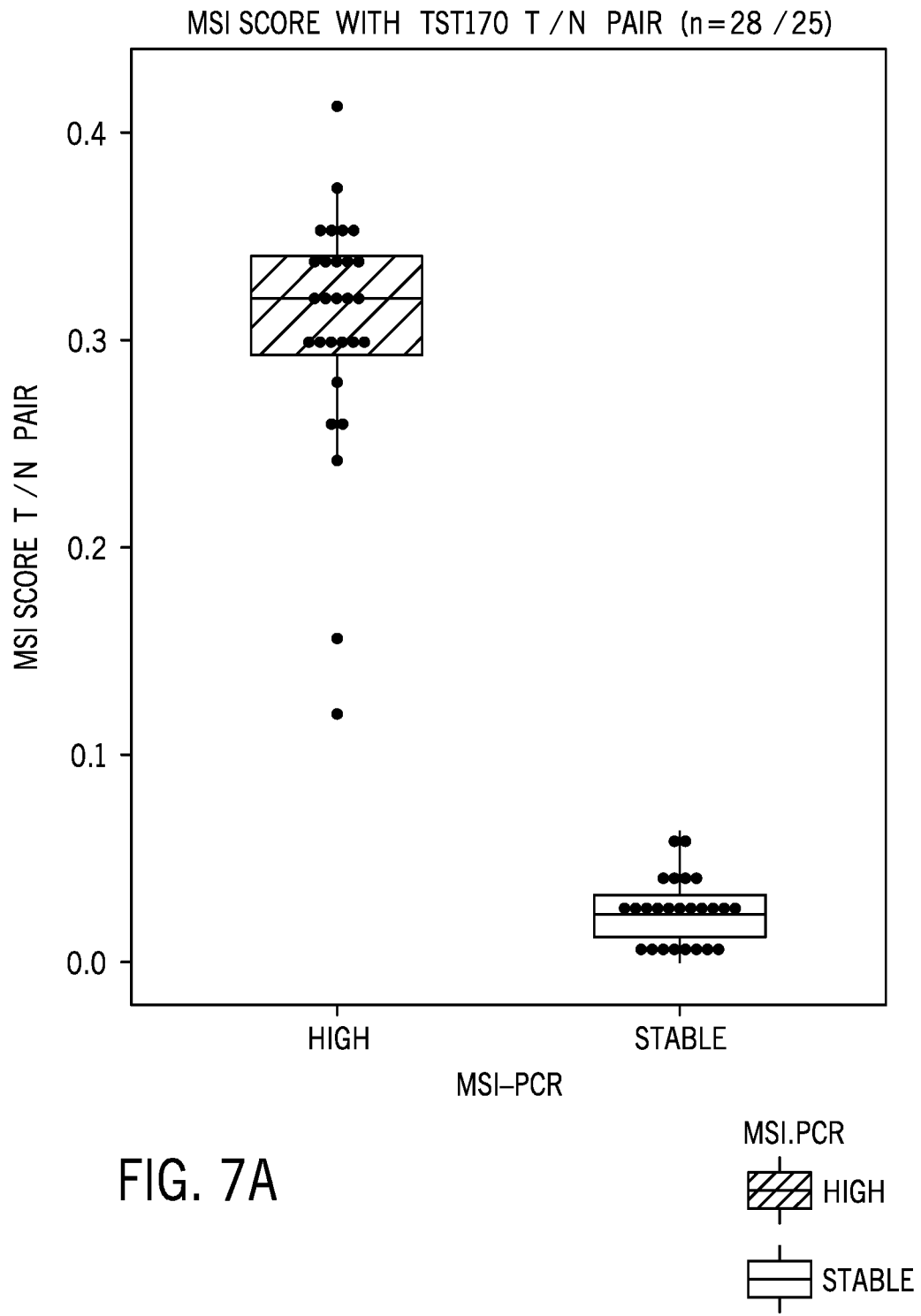
FIG. 7A is boxplot of a microsatellite instability score based on tumor/normal pairs.
Figure 7B:
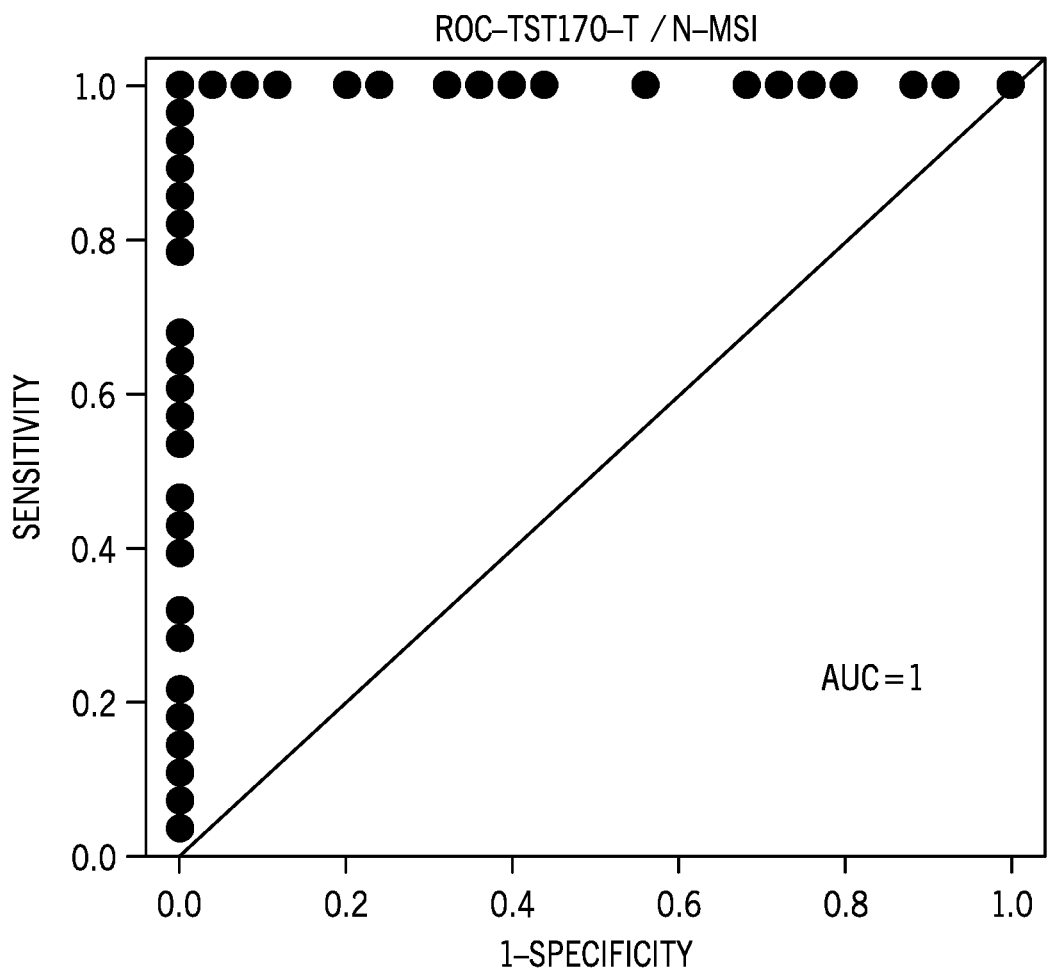
FIG. 7B is an ROC curve for tumor/normal pairs.
Figure 7C:
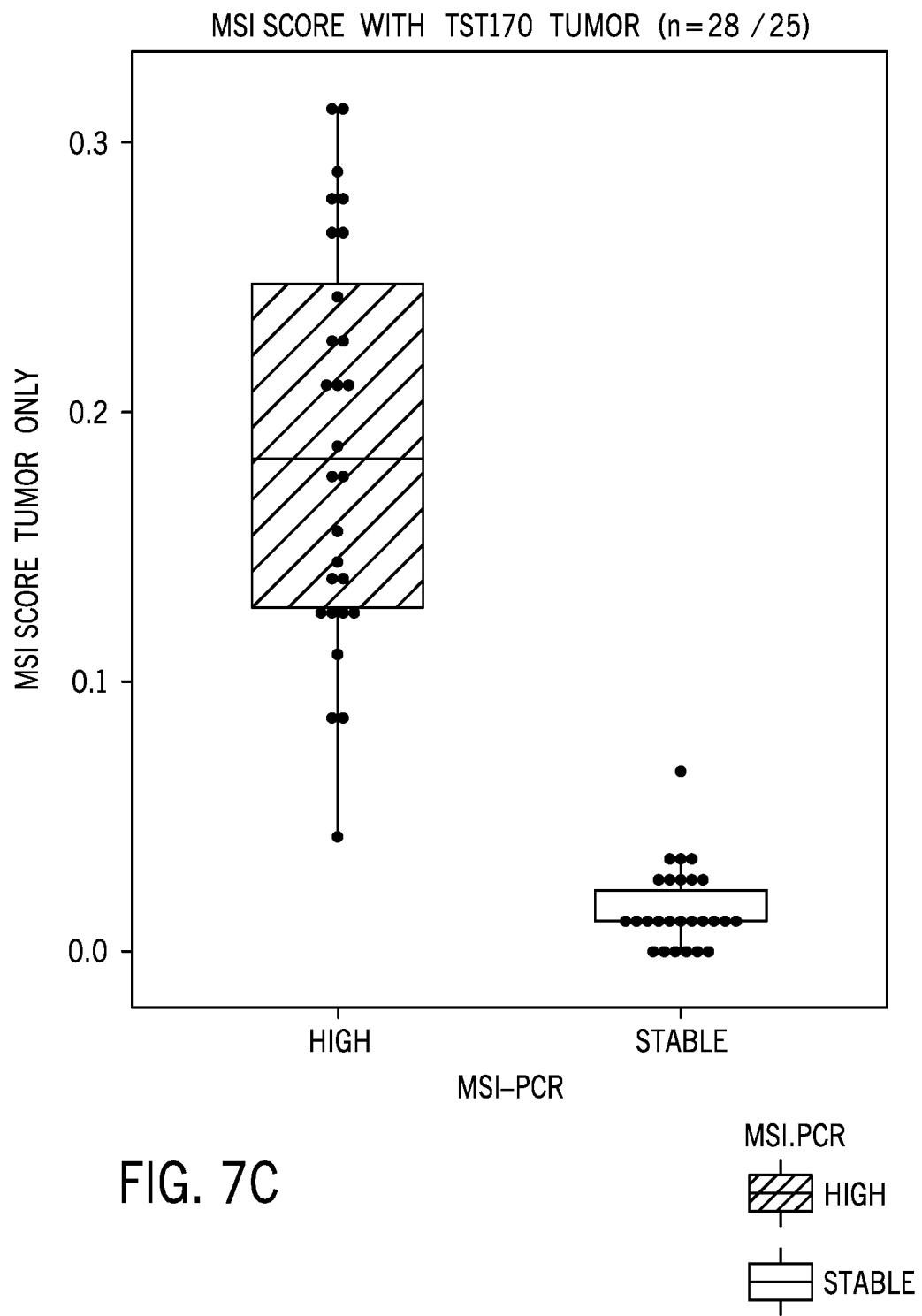
FIG. 7C is boxplot of a microsatellite instability score based on tumor only samples.
Figure 7D:
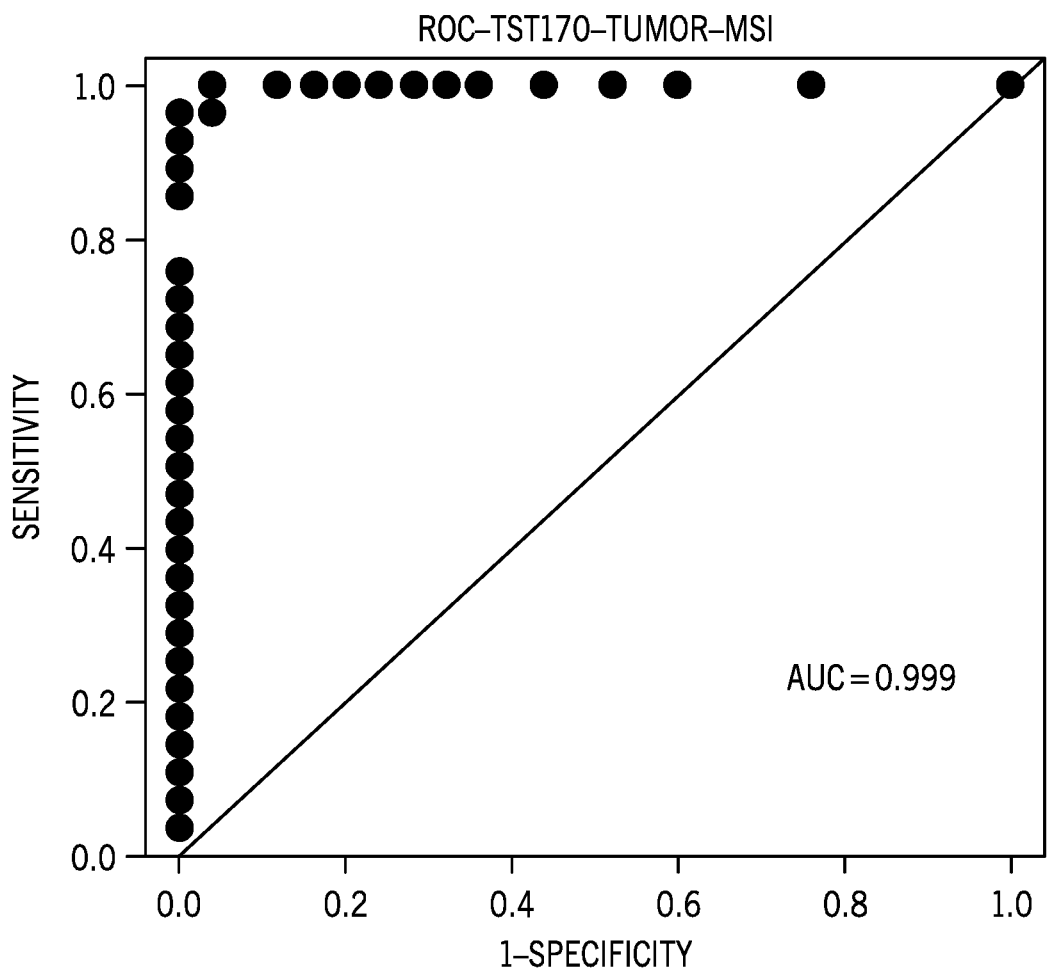
FIG. 7D is an ROC curve for tumor only samples.
Figure 7E:
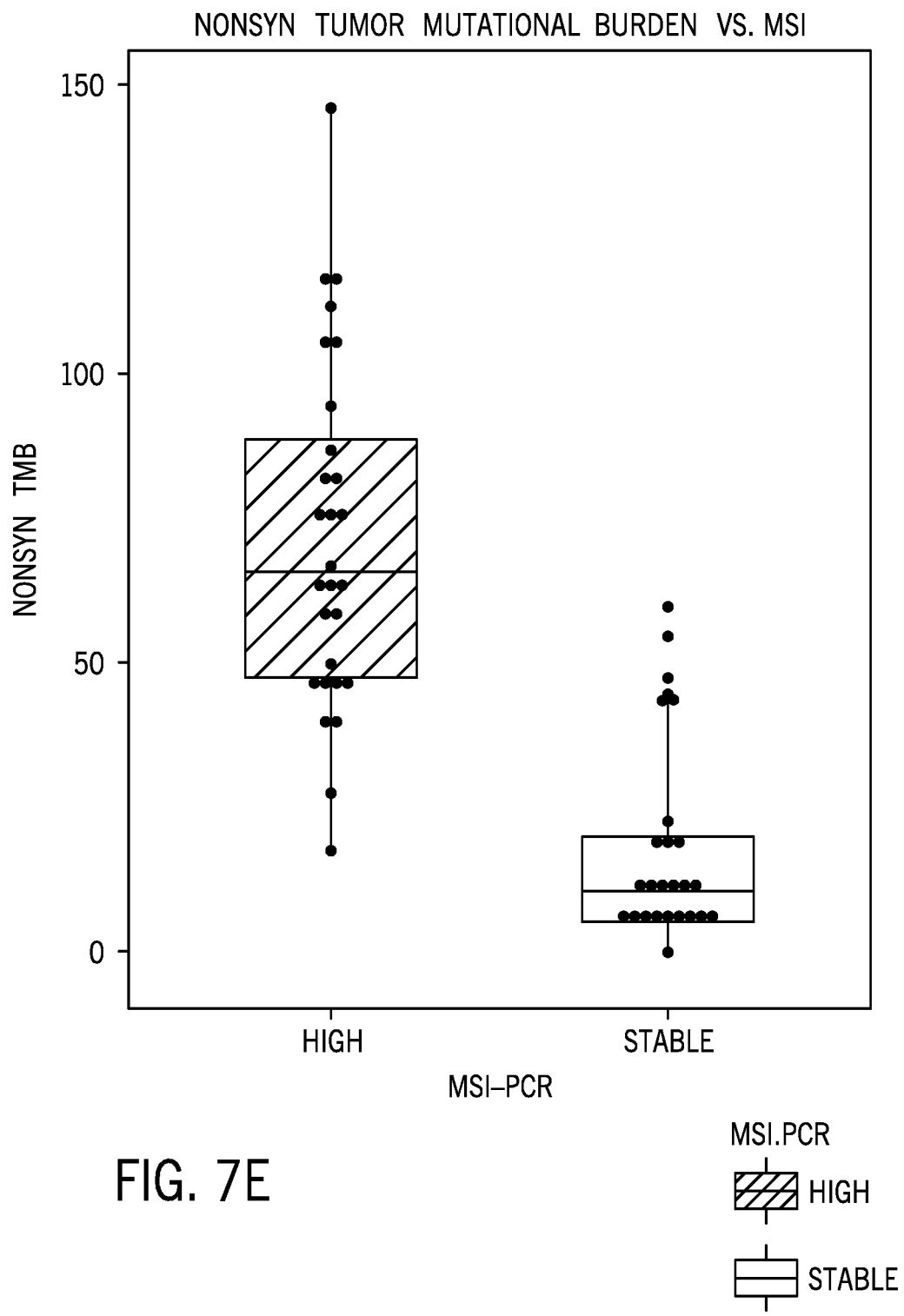
FIG. 7E is a boxplot showing MSI-H samples with higher nonsynonymous tumor mutational burden (TMB) compared to MSS samples.

FIG. 7A is boxplot of a microsatellite instability score based on tumor/normal pairs. FIG. 7B is an ROC curve for tumor/normal pairs. FIG. 7C is boxplot of a microsatellite instability score based on tumor only samples. FIG. 7D is an ROC curve for tumor only samples. FIG. 7E is a boxplot showing MSI-H samples with higher nonsynonymous tumor mutational burden (TMB) compared to MSS samples.

Figure 8A:
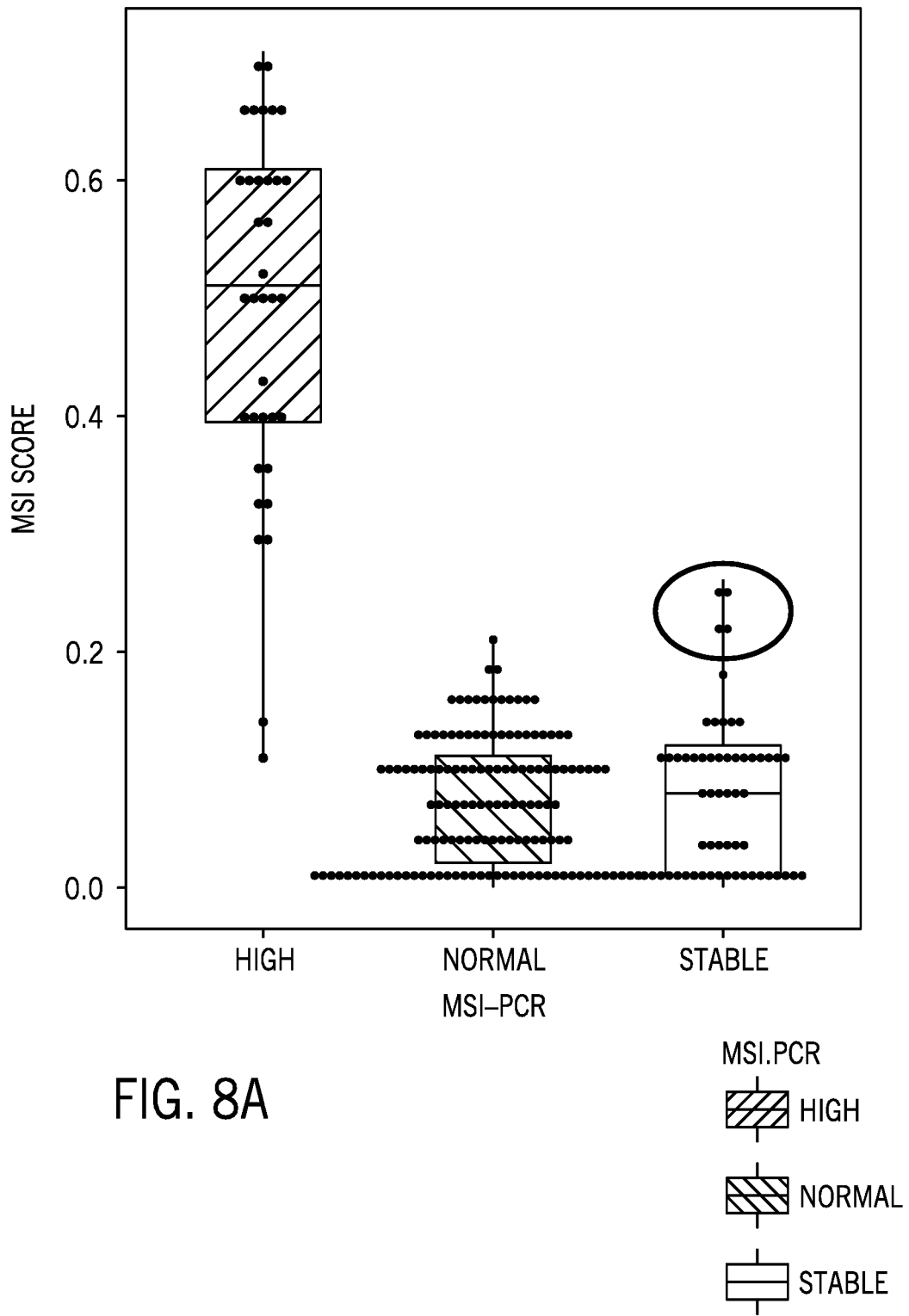
FIG. 8A is boxplot of a microsatellite instability score for 232 tumor/normal samples from a variety of tissue types and using a 58 sample normal colorectal cancer reference sample dataset matched to some of the tumor samples, with the red circled portion indicating false positives for MSI-H status per previous characterization as MSS based on MSI-PCR.

FIG. 8A is boxplot of a microsatellite instability score for 232 tumor/normal samples from a variety of tissue types and using a 58 sample normal colorectal cancer reference sample dataset matched to some of the tumor samples. The 58 sample normal colorectal cancer reference sample dataset was generated from the matched normal samples for the MSI-H and MSS CRC samples below. The samples included matched tumor normal pairs: n=140, with 92 pairs with MSI-PCR results:

MSI-H tumor: n=35 (32 CRC and 3 UCEC)
MSS tumor: n=57 (26 CRC and 31 UCEC)
Total test sample (92 tumor+140 normal=232 samples)

The samples were characterized as MSI-H (n=35), MSS (n=54) tumor, or normal (n=140) based on MSI-PCR. The microsatellite instability score was determined as provided herein. While the results generally aligned with the MSI-PCR results, the red circled portion indicates false positives for MSI-H based on the MSI cutoff score.

Figure 8B:
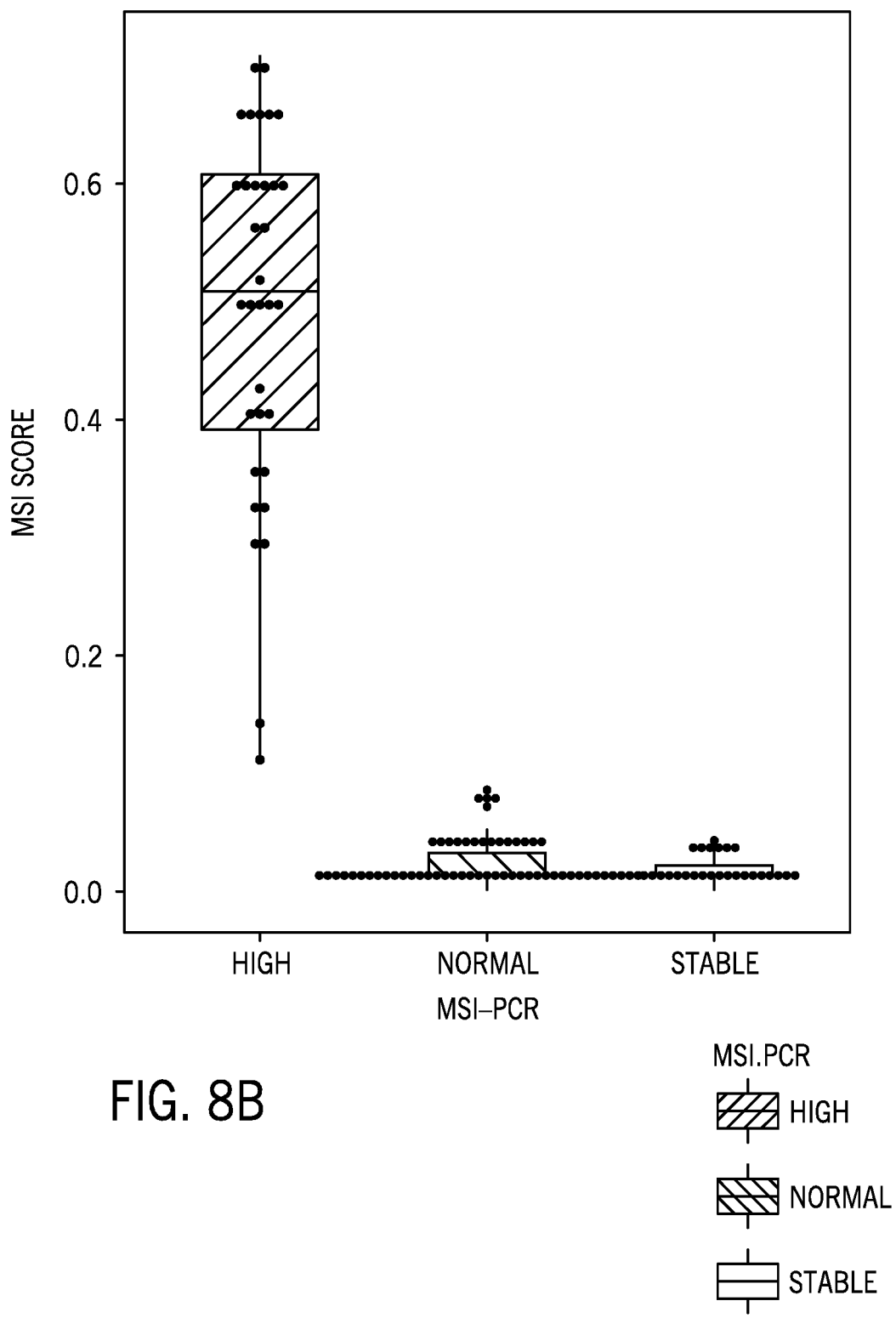
FIG. 8B is boxplot of a microsatellite instability score for 116 colorectal cancer matched tumor/normal samples using the 58 sample matched normal colorectal cancer reference sample dataset.

FIG. 8B is boxplot of a microsatellite instability score for the 58 colorectal cancer matched tumor/normal samples using the 58 sample matched normal colorectal cancer reference sample dataset of FIG. 8A and showing a tighter grouping of the stable-identified MSI scores.

Figure 9:
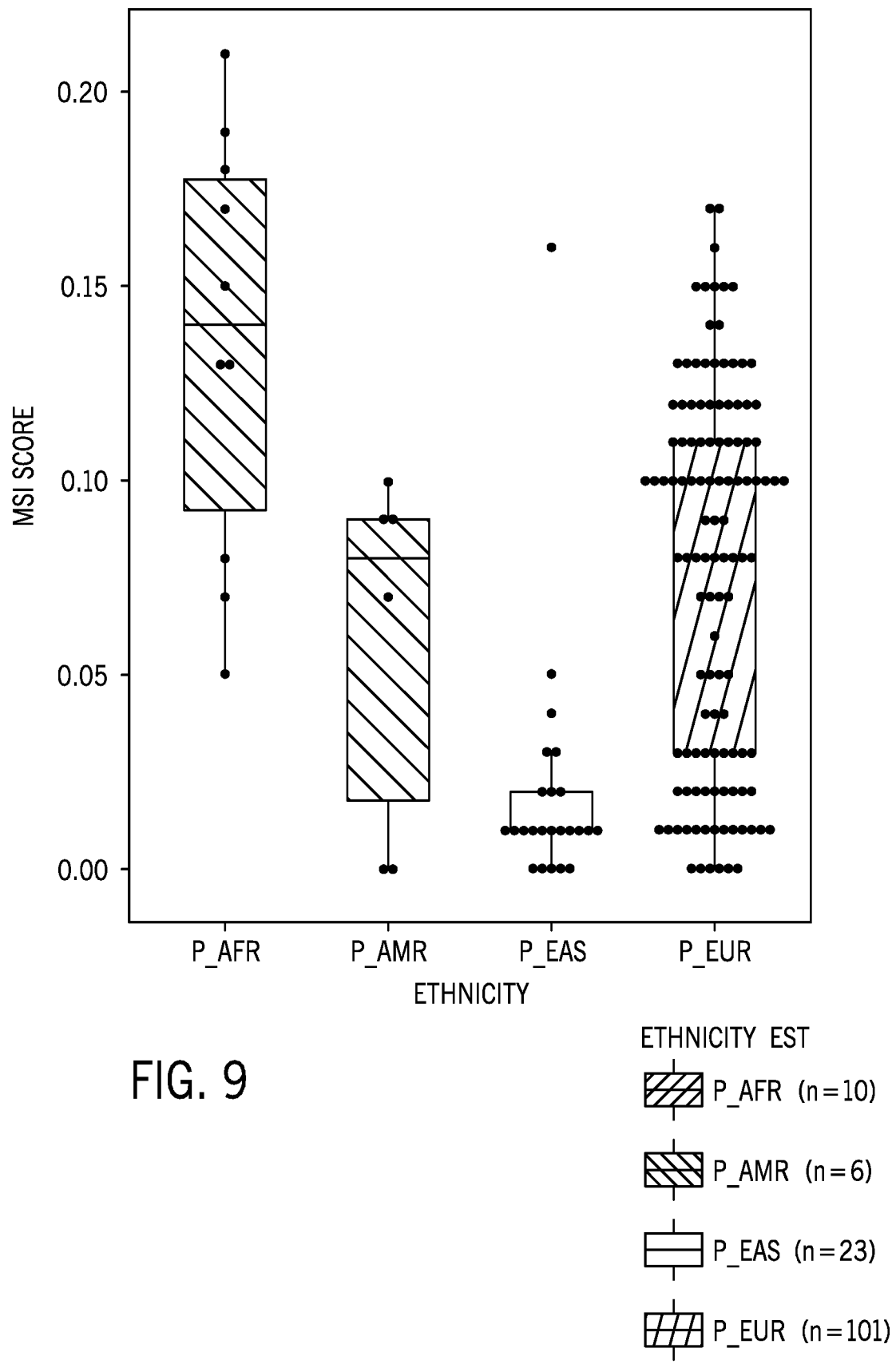
FIG. 9 is boxplot of a microsatellite instability score for 140 normal samples including samples from individuals associated with one of four different ethnic groups (African, South American, East Asian, and European) using the 58 sample normal colorectal cancer reference sample dataset.

FIG. 9 is boxplot of a microsatellite instability score for 140 normal samples whereby samples from individuals are separated into their associated ethnic groups (African, South American, East Asian, and European) using the 58 sample normal colorectal cancer reference sample dataset of FIG. 8A. As shown, the microsatellite instability scores vary between ethnic groups, indicating the potential for ethnic bias to be present into the reference sample dataset.

Figure 10:
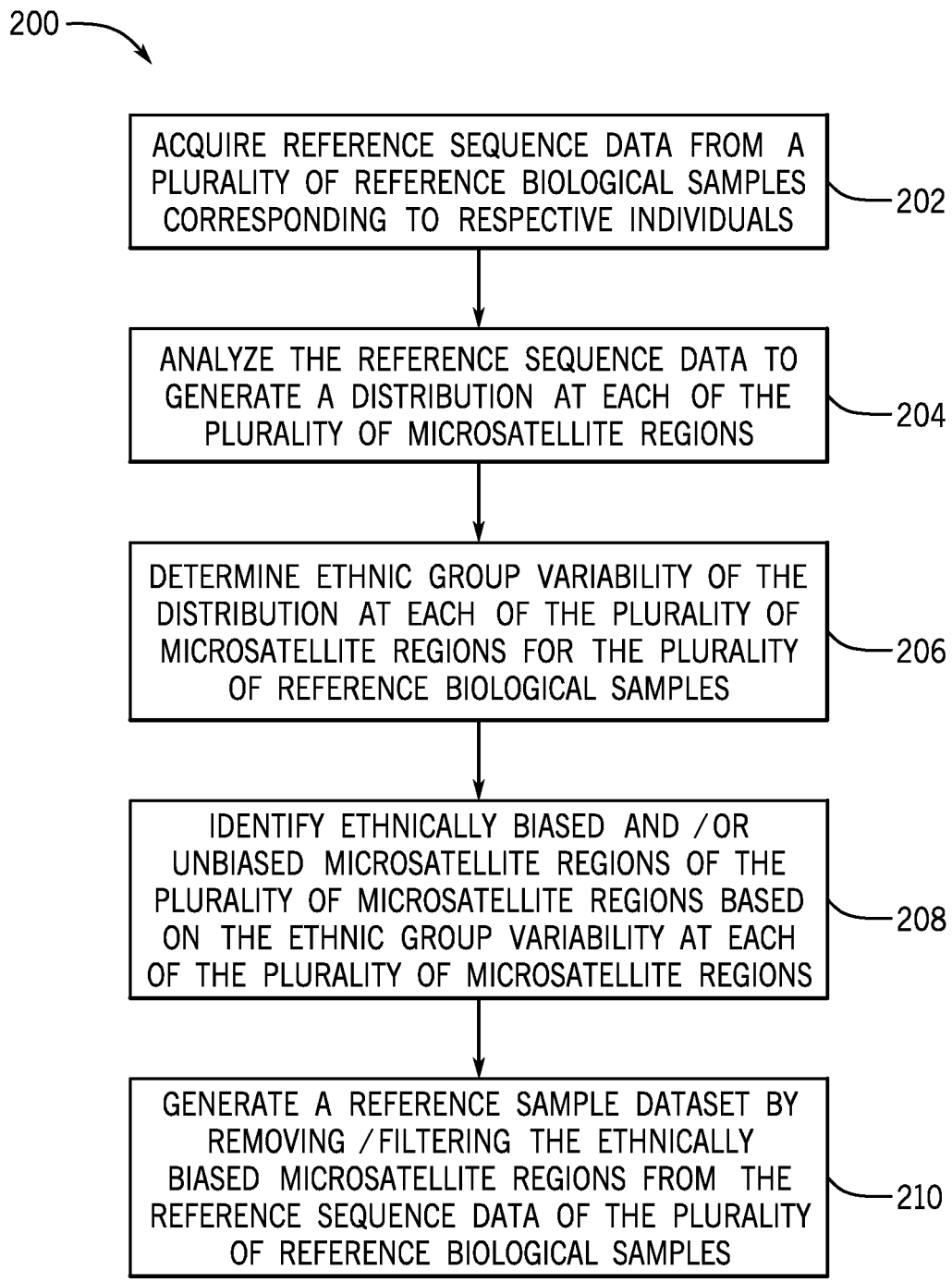
FIG. 10 is a flow diagram of a method of removing bias based on ethnic variability from a reference sample dataset.

FIG. 10 is a flow diagram of a method 200 of removing bias based on ethnic variability from a reference sample dataset. At step 202, reference sample sequence data may be acquired from reference samples of a cohort of a plurality of individuals, e.g., using a sequencing device 60 as provided herein. The plurality of individuals may be associated with a particular ethnic background (e.g., African, South American, East Asian, and European, in a non-limiting example). The association may be based on self-reporting, in one example. In other embodiments, previously acquired reference sample sequence data may be accessed. At step 204, the reference sequence data is analyzed to generate a distribution at each of a plurality of microsatellite regions of interest. In an initial quality control step, data for an individual microsatellite region from an individual reference sample having insufficient read coverage (e.g., fewer than 20 reads of a particular microsatellite region) may be filtered out of the reference sample sequence data (e.g., deleted, masked, or otherwise indicated as being not for consideration in further analysis steps).

At step 206, the ethnic group variability of the distribution (e.g., the allele distribution) at each of the plurality of microsatellite regions for the plurality of reference biological samples is determined. For example, for each of the individual reference sample sequence (e.g., 10 sequences, 20 sequences, or more) for which ethnic background information is available, the sequence data is grouped into one of the ethnic groups represented in the cohort for analysis. It should be understood that the cohort may be selected to provide an advantageous mix of samples from a desired number of ethnic groups that may be generally evenly distributed or may unevenly distributed in the cohort. The ethnic variability may include a variability between a first distribution of the sequence data of the group of samples associated with a first ethnic group relative to a second distribution of the sequence data of the group of samples associated with a second ethnic group. The distribution may be a region-by-region distribution, such that the variability between two or more ethnic groups at each individual microsatellite region for which sequence data is available (e.g., after any quality assessments) is assessed. In one embodiment, after the first quality assessment of sufficient coverage, certain individual microsatellite regions may fail to qualify for an assessment of ethnic variability based on a low number of qualifying samples. That is, the method may include a cutoff of samples (e.g., 5 or more individual samples of sufficient quality or having sufficient read coverage) per ethnic group to qualify for variability assessment.

At step 208, ethnically biased and/or unbiased microsatellite regions of the plurality of microsatellite regions are identified based on the ethnic group variability at each of the plurality of microsatellite regions for a group of reference samples separated into each individual ethnic group. In one embodiment, a measure of the variability of a microsatellite region sequence data distribution for a particular microsatellite region within a particular ethnic group is determined. This variability is then compared with variability of another ethnic group. This variability is then compared with variability of another ethnic group. Microsatellite regions with relatively large differences in variability between ethnic groups may be indicative of inherent ethnic variability for the region. The variability may be assessed by any suitable method, e.g., range, mean, variance and/or standard deviation or by Jensen-Shannon distance as provided herein. After this analysis is performed for each microsatellite region, the regions having a variability metric above a threshold may be identified as having high ethnic bias or variability while the regions having the variability metric below the threshold may be identified as having low or acceptable ethnic bias or variability. At step 210, a reference sample dataset is generated from the reference sequence data by removing/filtering the ethnically biased microsatellite regions from the reference sequence data of the plurality of reference biological samples. As a result of the method 200, the reference sample dataset is generated in which, for example, a portion of the sequenced microsatellite regions are excluded from further analysis because of identification of ethnic bias. The remaining microsatellite regions are less susceptible to bias related to ethnic background. Accordingly, the reference sample dataset has been made more robust and independent of bias to more accurately serve as a hypothetical matched normal to a wide range of samples of interest.

Figure 11A:
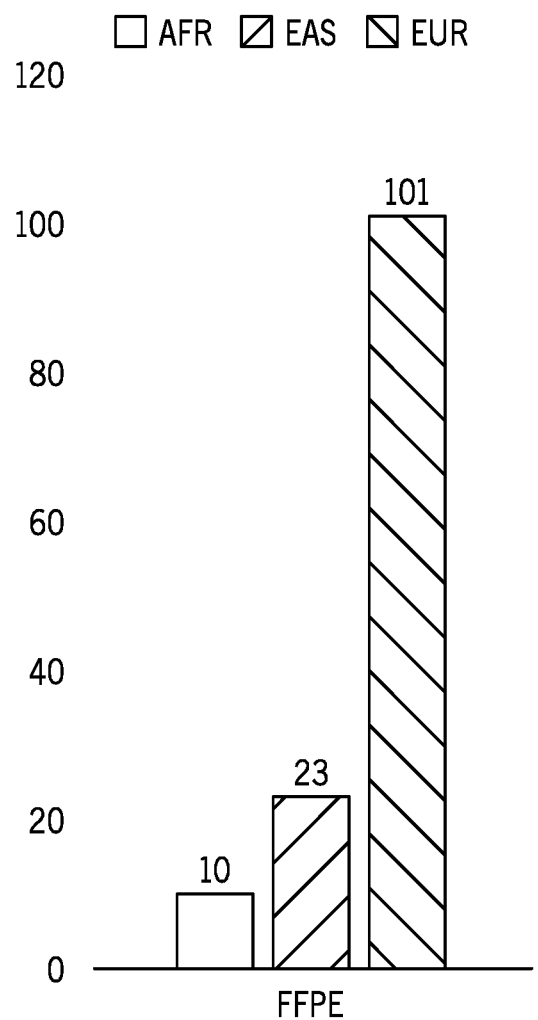
FIG. 11A shows the distribution of ethnicities in 140 samples used to assess ethnic variability in a reference sample dataset.
Figure 11B:
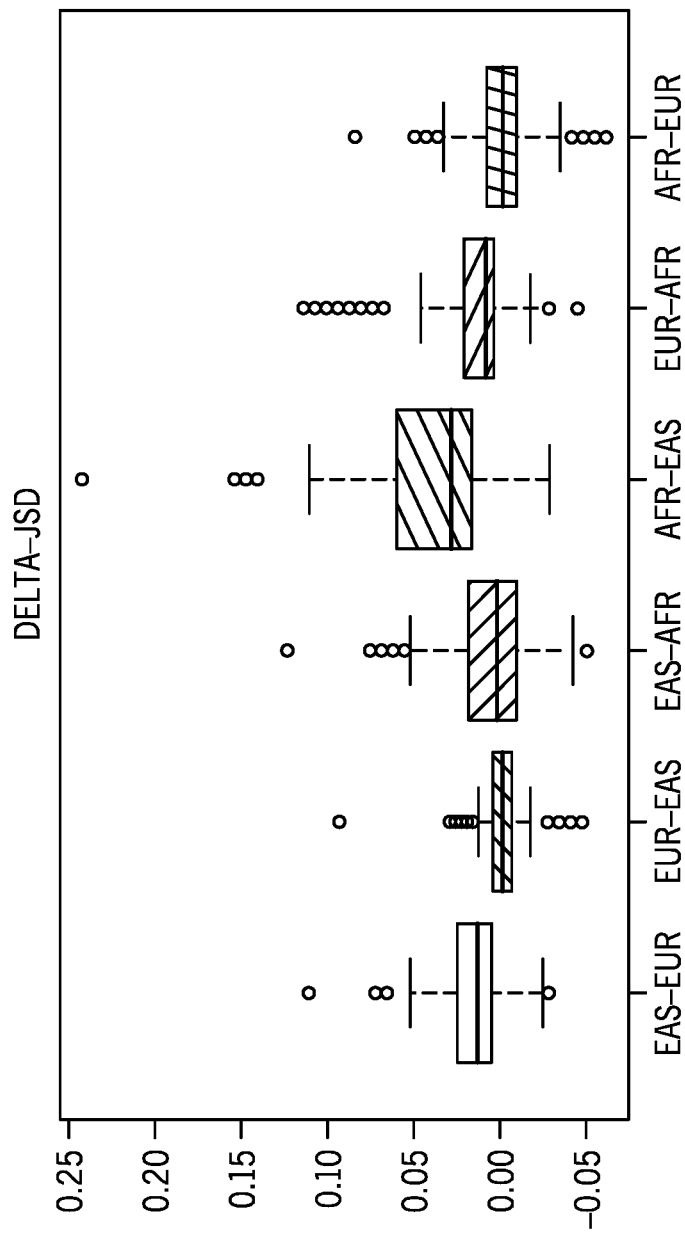
FIG. 11B shows results from an example technique of identifying microsatellite regions with relatively high ethnic variability in a reference sample dataset using calculated delta Jensen Shannon distances.

FIG. 11A shows the distribution of ethnicities in 140 samples used to assess ethnic variability in the reference sample dataset. FIG. 11B shows results from an example technique of identifying microsatellite regions with relatively high ethnic variability in a reference sample dataset using calculated delta Jensen Shannon distances. The delta Jensen Shannon distances were determined as follows:

$$\Delta JSD = \text{avg}(JSD_{between}) - \text{avg}(JSD_{within})$$

The delta Jensen Shannon distance for each microsatellite region is a measure of the average Jensen Shannon distance between two groups and the average Jensen Shannon distance within a group. A pair-wise comparison between three or more groups may be performed. The technique assessed 175 sites (microsatellite regions) with at least 20 supporting reads for minimum 5 samples of each ethnicity group. Based on the analysis, 44 sites with $>=0.1$ $\Delta JSD$ based on pair-wised comparison between three ethnicity groups were identified as having high ethnic variability. These sites were filtered out of (e.g., eliminated or masked from) the sequence data used to generate the reference sample dataset.

FIG. 12 is boxplot of a microsatellite instability score for 140 normal samples including samples from individuals associated with one of four different ethnic groups (African, South American, East Asian, and European) using the 58 sample normal colorectal cancer reference sample dataset with the identified microsatellite regions with relatively high ethnic variability filtered out of the reference sample dataset prior to the analysis. Compared to FIG. 9, which shows the same analysis, but without the filtering out of the identified microsatellite regions, the MSI scores are more compressed for certain ethnic groups, indicating the effect of the filtering out of the relatively high ethnic variability regions.

FIG. 13 is boxplot of a microsatellite instability score of 232 tumor/normal samples from a variety of tissue types using the 58 sample normal colorectal cancer reference sample dataset post filtering with the red circle denoting potential false positives. The MSI-H samples have generally intact MSI scores post filtering while normal/MSS samples have lower MSI scores. FIG. 14 is boxplot of a microsatellite instability score for normal samples associated with one of four different ethnic groups (African, South American, East Asian, and European) using 58 unmatched cell lines samples as the reference sample dataset pre and post filtering of the identified microsatellite regions with relatively high ethnic variability. The 58 unmatched cell lines included 10 IHW and 48 coriell lines with the following ethnic group distributions:

P_AFR (n=22) (African)
P_AMR (n=25) (South American)
P_EUR (n=8) (European)
P_EAS (n=3) (East Asian)

FIG. 15 is a comparison of the ethnic diversity of the unmatched cell lines samples reference dataset with the normal colorectal cancer reference sample dataset. The cell line reference sample does not share a genotype with FFPE samples, which were matched to a portion of the CRC tumor samples. The cell line reference sample dataset represents a true unmatched sample. Further, the cell line reference sample dataset represents different ethnicity composition from the original baseline or FFPE samples in general.

FIG. 16A is boxplot of a microsatellite instability score of 232 tumor/normal samples from a variety of tissue types using the unmatched cell lines samples as the reference sample dataset post filtering of the identified microsatellite regions with relatively high ethnic variability. FIG. 16B shows the sensitivity and specificity of the results of FIG. 16A.

FIG. 17 is a comparison of an original and repeat run of 78 colorectal cancer samples.

FIG. 18-19 show MSI score results correlation for reference sample datasets with varying numbers of samples. Performance was tested with random 10, 20, 30, 40, 50 baseline samples (randomly selected from 71 samples (58 cell lines+13 FFPE normal) that is not overlapped with the current 232 testing set).

FIG. 20 shows MSI scores for different titration levels of cell lines, and FIG. 21 is boxplot of a microsatellite instability score of 46 cell line samples including four MSI-H cell lines.

The results showed that blocking 44 ethnicity specific/biased sites improved performance. Further, reference sample datasets do not need to be sample type/ethnicity constrained. The performance was robust with $n>=30$ samples in the reference sample dataset.

A subset of available microsatellite sites may be selected of the available sites to develop a more sensitive limit of detection. Stringency in MSI site selection may improve limits of detection. FIG. 22 shows a cell line titration and associated limit of detection of MSI scores for various titrated levels of Lovo cells titrated into a cell line with microsatellite stability. FIG. 23 shows a cell line titration and associated limit of detection of MSI scores for various titrated levels of SW48 cells titrated into a cell line with microsatellite stability. The model of titration of cell lines in stable cells models the presence of tumor cells mixed with other cell types in a tumor sample. The depicted correlation between titration and loss of detection of MSI is based on an analysis of distribution of 100+ microsatellite sites and is limited by sequencing depth for the sample. While the depicted 2.5% or 5% titration at the limit of detection may be acceptable for solid samples, the detection of microsatellite instability in plasma (e.g., plasma DNA debris) may involve lower detection limits for accuracy.

However, in certain embodiments, a quality analysis of the available microsatellite sites may facilitate selection of a subset of sites with higher quality or lower variability to achieve improved limits of detection. With potential different DNA extraction methods, baseline, sequencing depth, microsatellite site quality may vary based on sample type (e.g., solid or FPE vs. liquid). FIG. 24 shows improved limits of detection for Lovo cells titrated into a cell line with microsatellite stability. FIG. 25 shows improved limits of detection for SW48 cells titrated into a cell line with microsatellite stability. FIGS. 24-25 represent analysis using only a subset of higher quality microsatellite sites, in the depicted example 16 out of 130 available sites. The sites of the reference dataset were selected as the lowest delta distribution at each individual site as assessed in the reference sequence data. Accordingly, in certain embodiments, the limit of detection is improved 5-fold by limiting the MSI sites to a subset of higher quality sites, e.g., using a ranking of the delta distribution and selecting those sites having a lowest distribution.

Further, the selection of the subset of MSI sites may be based on one or more user inputs and/or sample type. For samples, such as solid samples, a limit of detection achieved using all or most available MSI sites may be sufficient. Accordingly, indication of a solid sample may initiate analysis as provided herein using a larger subset of the available MSI sites than for a user input that the sample is a plasma or liquid sample. Further, the user may be able to input stringency or limit of detection settings in the sequencing or analysis device.

Technical effects of the disclosed embodiments include improved and more accurate microsatellite instability assessment for unmatched samples of interest. Additional technical effects include improved generation of reference sample datasets to serve as hypothetical matched normal samples for analysis of tumor only samples. The improved reference sample datasets used to determine the microsatellite instability score of an unmatched sample of interest are stripped of (e.g., via masking or eliminating) sites with high inter-ethnic group variability. In this manner, the reference sample dataset may be used as a hypothetical matched sample independent of the ethnic background of the individual associated with the unmatched sample of interest, providing a more robust technique for microsatellite instability assessment.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A computer-implemented method, comprising:
acquiring, using a microprocessor, genomic reference sequence data from a plurality of reference biological samples corresponding to respective individuals;
analyzing the reference sequence data to generate a distribution of sequences at each of a plurality of microsatellite regions;
determining ethnic group variability of the distribution at each of the plurality of microsatellite regions for the plurality of reference biological samples, the ethnic group variability including genomic sequence differences;
identifying ethnically biased microsatellite regions of the plurality of microsatellite regions based on the ethnic group variability at each of the plurality of microsatellite regions;
generating a reference sample dataset by removing or filtering the ethnically biased microsatellite regions from the reference sequence data of the plurality of reference biological samples, wherein reference sequence data is assessed based on having a depth of sequencing of at least 20 reads prior to inclusion in the hypothetical reference sample sequence;
assessing microsatellite instability based on a comparison of sequence data from a sample of interest to the hypothetical reference sample sequence, wherein the sample of interest is derived from a tumor sample of an individual and wherein a matched normal sample from the individual to the sample of interest is not available; and
determining that microsatellite instability for the sample of interest is classified as microsatellite instability high (MSI-H) or mismatch repair deficient (dMMR) and, based on such a classification, causing an immune checkpoint inhibitor to be administered to the individual.

2. The computer-implemented method of claim 1, wherein the sample of interest is associated with information comprising sample of interest origin information, wherein a plurality of hypothetical reference sample sequences, of which the hypothetical reference sequence is one, differ from one another based on origin, and wherein the hypothetical reference sample sequence is selected based on a match between the sample of interest origin information and the origin of the associated hypothetical reference sample sequence.

3. The computer-implemented method of claim 2, wherein the hypothetical reference sample sequence is generated from FFPE samples from a plurality of individuals and the sample of interest is an FFPE sample.

4. The computer-implemented method of claim 2, wherein the hypothetical reference sample sequence is generated from fresh frozen samples from a plurality of individuals and the sample of interest is a fresh frozen sample.

5. The computer-implemented method of claim 2, wherein the hypothetical reference sample sequence is generated from cell lines from a plurality of individuals and the sample of interest is a cell line.

6. The computer-implemented method of claim 2, wherein the sample information comprises tissue type information, wherein the plurality of hypothetical reference sample sequences differ from one another based on tissue type, and wherein the hypothetical reference sample sequence is further selected based on a match between the tissue type information and the tissue type of the hypothetical reference sample dataset.

7. The computer-implemented method of claim 2, wherein the sample information comprises sequencing panel information used to generate the sequence data, wherein the plurality of hypothetical reference sample sequences differ from one another based on a sequencing panel used to generate the reference sample datasets, and wherein the hypothetical reference sample sequence is further selected based on a match between the sequencing panel information and the sequencing panel used to generated the hypothetical reference sample sequence.

8. The computer-implemented method of claim 1, wherein assessing microsatellite instability comprises:
generating a quantitative microsatellite instability score by comparing a distance between a distribution at each microsatellite region between the sample of interest and the hypothetical reference sample sequence, wherein the number of microsatellite regions used to generate the quantitative microsatellite instability score is 5 or more, and wherein assessing microsatellite instability for the sample of interest is based on the quantitative microsatellite instability score.

9. The method of claim 1, further comprising:
acquiring second reference sequence data from a second plurality of reference biological samples corresponding to respective individuals; and
removing the ethnically biased microsatellite regions from the second reference sequence data to generate a second hypothetical reference sample dataset.

10. The method of claim 1, wherein the plurality of reference biological samples are derived fro normal tissue that is not from the individual.

11. The computer-implemented method of claim 1, wherein the comparison of sequence data from the sample of interest to the hypothetical reference sample sequence is based on a sample type of the tumor sample.

12. The computer-implemented method of claim 1, wherein the comparison of sequence data from the sample of interest to the hypothetical reference sample sequence is based on a cancer type of the tumor sample.

13. The computer-implemented method of claim 1, wherein the comparison of sequence data from the sample of interest to the hypothetical reference sample sequence is based on a ranking of a distance of respective distributions of individual microsatellite regions of the plurality of microsatellite regions.

14. The computer-implemented method of claim 1, wherein sequence data from each individual of the different respective individuals is assessed based on having a depth of sequencing of at least 20 reads prior to inclusion in the respective hypothetical reference sample sequence.

\* \* \* \* \*

UNITED STATES PATENT AND TRADEMARK OFFICE
CERTIFICATE OF CORRECTION

PATENT NO. : 12,154,664 B2
APPLICATION NO. : 16/191142
DATED : November 26, 2024
INVENTOR(S) : Shile Zhang et al.

It is certified that error appears in the above-identified patent and that said Letters Patent is hereby corrected as shown below:

On the Title Page

1. In Column 2 (Abstract), Line 12, replace "microsatelliate" with --microsatellite--

In the Claims

2. In Column 17, Line 39, Claim 1, after "to" insert --different--

3. In Column 17, Line 52, Claim 1, after "a" insert --hypothetical--

4. In Column 17, Line 52, Claim 1, replace "dataset" with --sequence--

5. In Column 18, Line 34, Claim 6, replace "dataset" with --sequence--

6. In Column 18, Line 59, Claim 9, after "to" insert --different--

7. In Column 18, Line 62, Claim 9, replace "dataset" with --sequence--

8. In Column 18, Line 64, Claim 10, replace "fro" with --from--

Signed and Sealed this
Sixth Day of May, 2025

Coke Morgan Stewart
*Acting Director of the United States Patent and Trademark Office*